US006083951A

United States Patent [19]
Bradbury

[11] Patent Number: 6,083,951
[45] Date of Patent: Jul. 4, 2000

[54] ARYL-SUBSTITUTED PYRIMIDINE SULPHONAMIDE COMPOUNDS AS ENDOTHELIN ANTAGONISTS

[75] Inventor: Robert Hugh Bradbury, Macclesfield, United Kingdom

[73] Assignee: Zeneca Limited, United Kingdom

[21] Appl. No.: 09/211,231

[22] Filed: Dec. 14, 1998

Related U.S. Application Data

[62] Division of application No. 08/716,194, filed as application No. PCT/GB95/00702, Mar. 29, 1995, Pat. No. 5,861,401.

[30] Foreign Application Priority Data

Mar. 31, 1994 [GB] United Kingdom .................. 9406437
Oct. 26, 1994 [GB] United Kingdom .................. 9421548

[51] Int. Cl.$^7$ ........................ A01N 43/54; A61K 31/505; C07D 239/02
[52] U.S. Cl. ........................ 514/256; 514/274; 544/316; 544/318; 544/335
[58] Field of Search .................. 544/316, 318, 544/335; 514/256, 274

[56] References Cited

U.S. PATENT DOCUMENTS

| | | | |
|---|---|---|---|
| 5,270,313 | 12/1993 | Burri et al. ........................ | 514/252 |
| 5,292,740 | 3/1994 | Burri et al. ........................ | 514/256 |
| 5,302,718 | 4/1994 | Agback et al. ..................... | 544/235 |
| 5,420,129 | 5/1995 | Breu et al. ........................ | 514/252 |
| 5,464,853 | 11/1995 | Chan et al. ....................... | 514/378 |
| 5,514,691 | 5/1996 | Chan et al. ....................... | 514/312 |
| 5,668,137 | 9/1997 | Phillips et al. .................... | 514/255 |

FOREIGN PATENT DOCUMENTS

| | | |
|---|---|---|
| 510526 | 10/1992 | European Pat. Off. . |
| 526708 | 2/1993 | European Pat. Off. . |
| 558258 | 9/1993 | European Pat. Off. . |
| 569193 | 11/1993 | European Pat. Off. . |
| 601386 | 6/1994 | European Pat. Off. . |
| 626174 | 11/1994 | European Pat. Off. . |
| 640596 | 3/1995 | European Pat. Off. . |
| 682016 | 11/1995 | European Pat. Off. . |
| 702012 | 3/1996 | European Pat. Off. . |
| 61257960 | 11/1986 | Japan . |
| 2 295 616 | 6/1996 | United Kingdom . |
| WO 9009787 | 9/1990 | WIPO . |
| WO 9427979 | 12/1994 | WIPO . |
| WO 9526957 | 10/1995 | WIPO . |

OTHER PUBLICATIONS

R.D. Desai et al., "Studies in Sulphonamides: Part II. Preparation of N$^1$–Heterocyclic Substituted Sulphonamides from Alpha–naphthylamine and Evaluation of their Antibacterial Properties", *Jour. Indian Chem. Soc.*, pp. 115–118, vol. 46, No. 2, 1969.

R.D. Desai et al., "Studies in Sulphonamides: Part IV. Some N$^6$–Heterocyclic Sulphonamides from 2–Naphthylamine as possible Antibacterial Agents", *J. Indian Chem. Soc.*, pp. 411–414, vol. 46, No. 5, 1969.

P. Mamalis et al., "142. Some Heterocyclic N–Oxides", *J. Chem. Soc.*, pp. 703–705, 1950.

*Chemical Abstracts*, vol. 84, No. 15, 1976, 84:100672y.
*Chemical Abstracts*, vol. 100, No. 15, 1984, 100:131420t.
*Chemical Abstracts*, vol. 106, No. 17, 1987, 106:133792p (corresponds to JP61257960).

Himel et al., "Fluorescent Analogs of Insecticides and Synergists. Synthesis and Reactions of Active–Site–Directed Fluorescent Probes", *Journal Agr. Food Chem.*, vol. 19, No. 6, 1971, pp. 1175–1180.

Stein et al., The Discovery of Sulfonamide Endothelin Antagonists and the Development of the Orally Active ET$_A$ Antagonist 5–(Dimethylamino)–N–(3, 4–dimethyl–5–isoxazolyl)–1–naphthalenesul fonamide, *Journal of Medicinal Chemistry*, Feb. 4, 1994, vol. 37, No. 3, pp. 329–331.

Identification of a New Class of ET$_A$ Selective Endothelin Antagonists by Pharmacophore Directed Screening, *Biochemical and Biophysical Research Communications*, May 30, 1994, vol. 201, No. 1, pp. 228–234. Chan et al.

Pharmacological Characterization of Bosentan, a New Potent Orally Active Nonpeptide Endothelin Receptor Antagonist, *Journal Pharmacol. Exp. Therap.*, 1994, 270, 228–235, Clozel et al.

Pages copied from a book of abstracts provided in an International Business Communications Conference entitled "Endothelin Inhibitors—Advances in Therapeutic Application and Development", Philadelphia, PA, Jun. 9–10, 1994, 33 pages.

*Primary Examiner*—Mukund J. Shah
*Assistant Examiner*—Tamthom N. Truong
*Attorney, Agent, or Firm*—Kenneth F. Mitchell

[57] ABSTRACT

Pyrimidine sulphonamide compounds of the following formula, $$Q-\underset{\underset{O}{\|}}{\overset{\overset{O}{\|}}{S}}-NH-\underset{\underset{R^2}{}}{\overset{R^2}{\diagup}}\text{pyrimidine}-R^1$$

wherein Q is a naphthyl or biphenyl group either unsubstituted or substituted with A$^1$, and where A$^1$, R$^1$ and R$^2$ are a variety of alkyl, aryl and cyclic moieties, as described in the specification hereof, which compounds are useful for the treatment of diseases or medical conditions such as hypertension, pulmonary hypertension, cardiac or cerebral circulatory disease and renal disease.

13 Claims, No Drawings

ARYL-SUBSTITUTED PYRIMIDINE SULPHONAMIDE COMPOUNDS AS ENDOTHELIN ANTAGONISTS

This is a divisional of application Ser. No. 08/716,194 filed Sep. 30, 1996, now U.S. Pat. No. 5,861,401, which is a National Phase of PCT/GB95/0072 filed Mar. 29, 1995.

The present invention relates to novel nitrogen derivatives and, more particularly, to novel N-heterocyclyl sulphonamides, and pharmaceutically-acceptable salts thereof, which possess endothelin receptor antagonist activity. These compounds are of value whenever such antagonist activity is desired, such as for research tools within pharmacological, diagnostic and related studies or in the treatment of diseases or medical conditions including, but not limited to, hypertension, pulmonary hypertension, cardiac or cerebral circulatory disease and renal disease, in warm-blooded animals (including man), in which elevated or abnormal levels of endothelin play a significant causative role. The invention also relates to pharmaceutical compositions of the novel compounds (and their salts) for use in treating said diseases or medical conditions, and to processes for the manufacture of the novel compounds. The invention further relates to the use of the novel compounds in treating one or more of the said diseases or medical conditions. A method of treating one or more of the said diseases or medical conditions using said compounds is also provided.

The endothelins are a family of endogenous 21 amino acid peptides comprising three isoforms, endothelin-1, endothelin-2 and endothelin-3. The endothelins are formed by cleavage of the $Trp^{21}$-$Val^{22}$ bond of their corresponding proendothelins by a putative endothelin converting enzyme. The endothelins are among the most potent vasoconstrictors known and have a characteristic long duration of action. They exhibit a wide range of other activities including cell proliferation and mitogenesis, extravasation and chemotaxis, and also interact with a number of other vasoactive agents. They also have direct effects on the heart. Thus the biological profile of the endothelins is consistent with a pathophysiological role in the cardiovascular system. The endothelins also have actions on other physiological systems including the-airways, gastro-intestinal tract, reproductive system, kidney, liver, central nervous system, neuroendocrine system and the blood.

The endothelins are released from a range of tissue and cell sources including vascular endothelium, vascular smooth muscle, kidney, liver, uterus, airways, intestine and leukocytes. Release can be stimulated by hypoxia, shear stress, physical injury and a wide range of hormones and cytokines. Elevated endothelin levels have been found in a number of disease states in man including hypertension, pulmonary hypertension, pre-eclampsia, congestive heart failure, myocardial infarction, angina pectoris, acute and chronic renal failure, ischaemic stroke, subarachnoid haemorrhage, atherosclerosis, hypercholesterolaemia, cardiogenic and endotoxic shock, diabetes mellitus, Raynaud's disease, scleroderma, systemic sclerosis, Buerger's disease, rheumatoid arthritis, asthma, bronchitis, acute respiratory failure, liver cirrhosis, Crohn's disease, ulcerative colitis, certain cancers and after surgery.

In European patent applications, publication nos. 558258 and 569193 are described certain N-(isoxazolyl) sulphonamides which are referred to as endothelin receptor antagonists.

Although a number of endothelin receptor antagonists are known, there is a continuing need for alternative antagonists. The present invention is based in part on this need and on our discovery of the unexpected antagonism of the endothelin receptor by certain N-heterocyclyl sulphonamides.

According to one aspect of the invention there is provided a compound of the formula I (set out hereinafter, together vith the other chemical formulae indentified by Roman numerals) wherein Q is a naphthyl or biphenyl group;

$A^1$, $A^2$ and $A^3$ are attached to a phenyl or benzene ring of Q and are independently selected from hydrogen, (1–6C)alkyl, amino(1–6C)alkyl, hrydroxy(1–6C)alkyl, N-[(1–4C)alkyl]amino(1–6C)alkyl, N,N-[di(1–4C)alkyl]amino(1–6C)alkyl, (2–6C)alkenyl, (2–6C)alkynyl, halogeno(1–6C)alkyl, (1–6C)alkoxy, dihalogeno(1–6C) alkoxy, trihalogeno(1–6C)alkoxy, (2–6C)alkenyloxy, (1–4C)alkoxy(1–6C)alkyl, (1–4C)alkylthio(1–6C)alkyl, (1–4C)alkylsulphinyl(1–6C)alkyl, (1–4C)alkylsulphonyl (1–6C)alkyl, (1–4C)alkylenedioxy, (3–6C)cycloalkyl, (3–8C)cycloalkyl(1–6C)alkyl, phenyl, phenyl(1–6C) alkyl, phenoxy, phenyl(1–6C)alkoxy, halogeno, hydroxy, mercapto, cyano, nitro, carboxy, (1–6C)alkoxycarbonyl, (2–6C)alkenyloxycarbonyl, phenyloxycarbonyl, phenyl (1–6C)alkoxycarbonyl, (1–6C)alkanoyl, benzoyl, (1–6C) alkylthio, (1–6C)alkylsulphinyl, (1–6C)alkylsulphonyl, phenylthio, phenylsulphinyl, phenylsulphonyl, (1–6C) alkanoylamino, trifluoroacetyl, trifluoroacetamido, N-[(1–4C)alkyl]trifluoroacetamido, benzamido, N-[(1–4C)alkyl]benzamido, carbamoyl, (1–4C) alkylcarbamoyl, di-(1–4C)alkylcarbamoyl, phenylcarbamoyl, sulphamoyl, N-(1–4C) alkylsulphamoyl, N,N-di(1–4C)alkylsulphamoyl, N-phenylsulphamoyl, (1–6C)alkanesulphonamido, benzenesulphonamido, ureido, 3-(1–6C)alkylureido, 3-phenylureido, thioureido, 3-(1–6C)alkylthioureido, 3-phenylthioureido and a group —NRaRb in which Ra and Rb are independently selected from hydrogen, (1–6C) alkyl, phenyl(1–4C)alkyl and (1–6C)alkyl bearing a carboxy or (1–4C)alkoxycarbonyl group, or the group —NRaRb taken together complete a 1-pyrrolidinyl, 2-oxo-1-pyrrolidinyl, 1-piperidinyl or 2-oxo-1-piperidinyl ring;

W, X, Y and Z are independently selected from nitrogen and $CR^2$ such that two or three of W, X, Y and Z are nitrogen and the remainder are $CR^2$, or X is nitrogen and W, Y and Z are $CR^2$;

$R^2$ has any of the values defined above for $A^1$, $A^2$ or $A^3$;

$R^1$ is selected from (1–6C)alkyl, amino(1–6C)alkyl, hydroxy(1–6C)alkyl, N-[(1–4C)alkyl]amino(1–6C)alkyl, N,N[di (1–4C)alkyl]amino(1–6C)alkyl, (2–6C)alkenyl, 2-[(1–6C)alkoxycarbonyl]ethenyl, 2-phenylethenyl, (2–6C)alkynyl, (1–6C)alkoxycarbonylethynyl, phenylethynyl, halogeno(1–6C)alkyl, (1–3C)alkoxy, dihalogeno(1–3C)alkoxy, trihalogeno(1–3C)alkoxy, (2–6C)alkenyloxy, (1–4C)alkoxy(1–6C)alkyl, (1–4C) alkylthio(1–6C)alkyl, (1–4C)alkylsulphinyl(1–6C)alkyl, (1–4C)alkylsulphonyl(1–6C)alkyl, (3–6C)cycloalkyl, (3–8C)cycloalkyl(1–6C)alkyl, phenyl(1–6C)alkyl, phenyl(1–3C)alkoxy, halogeno, hydroxy, mercapto, nitro, carboxy, (1–6C)alkoxycarbonyl, (2–6C) alkenyloxycarbonyl, phenyloxycarbonyl, phenyl(1–6C) alkoxycarbonyl, (1–6C)alkanoyl, benzoyl, (1–6C) alkylthio, (1–6C)alkylsulphinyl, (1–6C)alkylsulphonyl, phenylthio, phenylsulphinyl, phenylsulphonyl, (1–6C) alkanoylamino, trifluoroacetyl, trifluoroacetamido, N-[(1–4C)alkyl]trifluoroacetamido, benzamido, N-[(1–4C)alkyl]benzamido, carbamoyl, (1–4C)

alkylcarbamoyl, di-(1–4C)alkylcarbamoyl, phenylcarbamoyl, sulphamoyl, N-(1–4C)alkylsulphamoyl, N,N-di(1–4C)alkylsulphamoyl, N-phenylsulphamoyl, (1–6C)alkanesulphonamido, benzenesulphonamido, ureido, 3-(1–6C)alkylureido, 3-phenylureido, thioureido, 3-(1–6C)alkylthioureido, 3-phenylthioureido and a group —NRaRb in which Ra and Rb are independently selected from hydrogen, (1–6C)alkyl, phenyl(1–4C)alkyl and (1–6C)alkyl bearing a carboxy or (1–4C)alkoxycarbonyl group, or the group —NRaRb taken together complete a 1-pyrrolidinyl, 2-oxo-1-pyrrolidinyl, 1-piperidinyl or 2-oxo-1-piperidinyl ring; or when X or Y is $CR^2$, $R^1$ together with the adjacent $R^2$ is (3–5C)alkylene or (3–5C)alkenylene which together with the carbon atoms to vhich $R^1$ and the adjacent $R^2$ are attached complete a 5–7 membered ring; and wherein any of said phenyl, naphthyl or benzene moieties of $A^1$, $A^2$, $A^3$, $R^1$ or $R^2$ may be unsubstituted or bear one or two substituents independently selected from (1–4C)alkyl, (1–4C)alkoxy, halogeno, cyano and trifluoromethyl; or a pharmaceutically-acceptable salt thereof.

It will be appreciated that, depending on the nature of the substituents, certain of the formula I compounds may possess one or more chiral centres and may be isolated in one or more racemic or optically active forms. It is to be understood that the present invention concerns any form of such a compound of formula I vhich possesses the aforementioned useful pharmacological properties, it being well known to make optically active forms, for example by synthesis from suitable chiral intermediates or by resolution, and how to determine their pharmacological properties, for example by use of the tests described hereinafter.

It will also be appreciated that a compound of formula I may exhibit polymorphism, that a compound of formula I may form a solvate and that a compound of formula I may exist in more than one tautomeric form. It is to be understood that the present invention also concerns any polymorphic form, any tautomer or any solvate, or any mixture thereof, which possesses endothelin receptor antagonist activity.

It is further to be understood that generic terms such as "alkyl" include both straight and branched chain variants when the carbon numbers permit.

However, when a particular radical such as "propyl" is given, it is specific to the straight chain variant, branched chain variants such as "isopropyl" being specifically named when intended. The same convention applies to other radicals.

It is further to be appreciated that in those ccompounds in which there may be more than one $R^2$ present, the value for each $R^2$ may be the same or different.

Particular values for $A^1$, $A^2$, $A^3$, $R^1$ or $R^2$, where appropriate include, by way of example, for (1–6C)alkyl: (1–4C)alkyl, such as methyl, ethyl, propyl, isopropyl and sec-butyl; for amino(1–6C)alkyl: amino(1–4C)alkyl, such as aminomethyl and 2-aminoethyl; for hydroxy(1–6C)alkyl: hydroxy(1–4C)alkyl, such as hydroxymethyl, 1-hydroxyethyl and 2-hydroxyethyl; for N-[(1–4C)alkyl]amino(1–6C)alkyl: N-[(1–2C)alkylamino(1–4C)alkyl, such as methylaminomethyl and methylaminoethyl; for N,N-[di(1–4C)alkyl]amino(1–6C)alkyl: N,N-[di(1–2C)alkyl]amino-(1–4C)alkyl, such as dimethylaminomethyl and 2-(dimethylamino)ethyl; for (2–6C)alkenyl: (2–4C)alkenyl, such as vinyl, allyl, 1-propenyl and 2-butenyl; for 2-[(1–6C)alkoxycarbonyl]ethenyl: 2-[(1–4C)alkoxycarbony]ethenyl, such as 2-methoxycarbonylethenyl and 2-ethoxycarbonylethenyl; for (2–6C)alkynyl: (2–4C)alkynyl, such as ethynyl, 1-propynyl, 2-propynyl and 1-butynyl; for (1–6C)alkoxycarbonylethynyl: (1–4C)alkoxycarbonylethynyl, such as methoxycarbonylethynyl and ethoxycarbonylethynyl; for halogeno(1–6C)alkyl: halogeno(1–4C)alkyl, such as chloromethyl, bromomethyl, fluoromethyl, dichloromethyl, difluoromethyl, trifluoromethyl, 2,2,2-trifluoroethyl and pentafluoroethyl; for (1–6C)alkoxy: (1–4C)alkoxy, such as methoxy, ethoxy, propoxy, isopropoxy and butoxy; for (1–3C)alkoxy: methoxy and ethoxy; for di- or tri-halogeno(1–6C)alkoxy: di- or trihalogeno(1–4C)alkoxy, such as difluoromethoxy, trifluoroethoxy, 2,2,2-trifluoroethoxy, 3,3,3-trifluoropropoxy and pentafluoroethoxy; for di- or trihalogeno(1–3C)alkoxy: difluoromethoxy, trifluoroethoxy and 2,2,2-trifluoroethoxy; for (2–6C)alkenyloxy: (2–4C)alkenyloxy, such as vinyloxy, allyloxy, 1-propenyloxy and 2-butenyloxy; for (1–4C)alkoxy(1–6C)alkyl: (1–2C)alkoxy(1–4C)alkyl, such as methoxymethyl, ethoxymethyl, 1-methoxyethyl, 2-methoxyethyl, 2-ethoxyethyl and 3-methoxypropyl; for (1–4C)alkylthio(1–4C)alkyl: methylthiomethyl, 1-methylthioethyl, 2-methylthioethyl, 2-methylthioprop-2-yl, ethylthiomethyl,1-ethylthioethyl, 2-ethylthioethyl and 2-ethylthioprop-2-yl; for (1–4C)alkylsulphinyl(1–4C)alkyl: methylsulphinylmethyl, 1-methylsulphinylethyl, 2-methylsulphinylethyl, 2-methylsulphinylprop-2-yl, ethylsulphinylmethyl, 1-ethylsulphinylethyl, 2-ethyl-sulphinylethyl and 2-ethylsulphinylprop-2-yl; for (1–4C)alkylsulphonyl(1–4C)alkyl: methylsulphonylmethyl, 1-methylsulphonylethyl, 2-methylsulphonylethyl, 2-methylsulphonylprop-2-yl, ethylsulphonylmethyl, 1-ethylsulphonylethyl, 2-ethyl-sulphonylethyl and 2-ethylsulphonylprop-2-yl; for (1–4C)alkylenedioxy: methylenedioxy, ethylenedioxy and isopropylidenedioxy; for (3–6C)cycloalkyl: cyclopropyl, cyclobutyl and cyclopentyl; for (3–8C)cycloalkyl(1–6C)alkyl: (3–5C)cycloalkyl(1–2C)alkyl, such as cyclopropylmethyl, cyclopropylethyl, cyclobutylmethyl and cyclopentylmethyl; for phenyl(1–6C)alkyl: phenyl(1–4C)alkyl, such as benzyl, 1-phenylethyl and 2-phenylethyl; for phenyl(1–6C)alkoxy: phenyl(1–4C)alkoxy, such as benzyloxy, 1-phenylethoxy, 2-phenylethoxy, 2-phenylpropoxy and 3-phenylpropoxy; for phenyl(1–3)alkoxy: benzyloxy, 1-phenylethoxy and 2-phenylethoxy; for halogeno: fluoro, chloro, bromo and iodo; for (1–6C)alkoxycarbonyl: (1–4C)alkoxycarbonyl, such as methoxycarbonyl, ethoxycarbonyl and propoxycarbonyl; for C2–6C)alkenyloxycarbonyl: allyloxycarbonyl, 2-methyl-2-propenyloxycarbonyl and 3-methyl-3-butenyloxycarbonyl; for phenyl(1–6C)alkoxycarbonyl: phenyl(1–4C)alkoxycarbonyl, such as benzyloxycarbonyl, 1-phenylethoxycarbonyl and 2-phenylethoxycarbonyl; for (1–6C)alkanoyl: (1–4C)alkanoyl, such as formyl, acetyl and propionyl; for (1–6C)alkylthio: (1–4C)alkylthio, such as methylthio and ethylthio; for (1–6C)alkylsulphinyl: (1–4C)alkylsulphinyl, such as methylsulphinyl and ethylsulphinyl; for (1–6C)alkylsulphonyl: (1–4C)alkylsulphonyl, such as methylsulphonyl and ethylsulphonyl; for (1–6C)alkanoylamino: (1–4C)alkanoylamino, such as formamido, acetamido and propionamido; for N-[(1–4C)alky]trifluoroacetamide: N-methyltrifluoroacetamide and N-ethyltrifluoroacetamide; for N-[(1–4C)alkyl]benzamido: N-methylbenzamido and N-ethylbenzamido; for (1–4C)alkylcarbamoyl: N-methylcarbamoyl and N-ethylcarbamoyl; for di(1–4C)alkylcarbamoyl: N,N-dimethylcarbamoyl and N,N-diethylcarbamoyl; for N-(1–4C)alkylsulphamoyl: N-methylsulphamoyl and N-ethylsulphamoyl; for N,N-di(1–4C)alkylsulphamoyl: N,N-dimethylsulphamoyl and N,N-diethylsulphamoyl; for (1–6C)alkanesulphonamido: (1–4C)alkanesulphonamido, such as methanesulphonamido and ethanesulphonamido; for 3-(1–6C)alkylureido: 3-(1–4C)alkylureido, such as 3-methylureido, 3-ethylureido and 3-propylureido; and for 3-(1–6C)alkylthioureido: 3-(1–4C)alkylthioureido, such as 3-methylthioureido, 3-ethylthioureido and 3-propylthioureido;

A particular value for $R^1$ together with an adjacent $R^2$ when it is (3–5C)alkylene or (3–5C)alkenylene includes, for example, trimethylene, tetramethylene, 1-propenylene and 2-propenylene.

A particular value for Ra or Rb includes, by way of example, for (1–6C)alkyl: (1–4C)alkyl, such as methyl, ethyl and propyl; for (1–6C)alkyl bearing a carboxy or (1–4C)alkoxycarbonyl group: (1–4C)alkyl bearing a carboxy or (1–2C)alkoxycarbonyl group, such as carboxymethyl, carboxyethyl, methoxycarbonylmethyl, methoxycarbonylethyl, ethoxycarbonylethyl, methoxycarbonylpropyl and ethoxycarbonylpropyl; and for phenyl (1–4C)alkyl: benzyl, 1-phenylethyl and 2-phenylethyl.

A particular value for a substituent on a phenyl, naphthyl or benzene moiety of $A^1$, $A^2$, $A^3$, $R^1$ or $R^2$ includes, by way of example, for (1–4C)alkyl: methyl and ethyl; for (1–4C)alkoxy: methoxy and ethoxy; and for halogeno: fluoro, chloro, bromo and iodo.

Particular combinations which W, X, Y and Z can take are as follows:

(a) when W and Z are both N, X and Y are both $CR^2$;
(b) when W and X are both N, Y and Z are both $CR^2$;
(c) when W and Z are both $CR^2$, and X and Y are both N;
(d) when W and Y are both $CR^2$, and X and Z are both N;
(e) when W, X and Z are all N, Y is $CR^2$;
(f) when W, X and Y are all N, Z is $CR^2$; and
(g) when X is nitrogen, W, Y and Z are all $CR^2$.

Within these combinations, (a), (b), (c), (d) and (g) are of particular interest, especially (b), (c) and (d) and more especially (b) and (d).

Particular values for Q are, for example, naphthyl (especially naphth-1-yl and naphth-2-yl) or ortho-biphenyl.

A group of values for $R^1$ of interest include, for example, (1–4C)alkyl, amino(1–4C)alkyl, hydroxy(1–4C)alkyl, N-(1–4C)alkylamino(1–4C)alkyl, N,N-di(1–4C)alkylamino(1–4C)alkyl, halogeno, halogeno(1–4C)alkyl, (2–6C)alkenyl, (2–6C)alkynyl, nitro, phenyl(1–4C)alkyl, (3–6C)cycloalkyl, (3–8C)cycloalkyl(1–4C)alkyl, (1–6C)alkanoylamino and a group —NRaRb in which Ra and Rb are independently selected from hydrogen, (1–4C)alkyl and phenyl(1–4C)alkyl.

A sub-group of values for $R^1$ of particular interest include, for example, halogeno (such as chloro, bromo and iodo), (1–4C)alkyl (such as methyl and ethyl), (1–3C)alkoxy (such as methoxy and ethoxy), (1–4C)alkylthio (such as methylthio and ethylthio) and (2–4C)alkynyl (such as ethynyl).

Values for $R^1$ which are preferred include, for example, halogeno, methyl, methoxy, ethoxy, methylthio, trifluoromethyl and nitro, particularly halogeno, methyl, methoxy and methylthio, and especially chloro, bromo and iodo.

A group of values for $R^2$ of interest include, for example, hydrogen, (1–4C)alkyl, amino(1–4C)alkyl, hydroxy(1–4C)alkyl, N-(1–4C)alkylamino(1–4C)alkyl, N,N-di(1–4C)alkylamino(1–4C)alkyl, (1–4C)alkoxy, halogeno, halogeno(1–4C)alkyl, nitro, phenyl(1–4C)alkyl, (1–6C)alkanoylamino and a group —NRaRb in which Ra and Rb are independently selected from hydrogen, (1–6C)alkyl and phenyl(1–4C)alkyl.

A sub-group of values for $R^2$ of particular interest include, for example, hydrogen, halogeno, (1–4C)alkoxy and (1–4C)alkyl, especially hydrogen, methyl, methoxy, chloro and bromo.

A group of values for $A^1$, $A^2$ or $A^3$ of interest include, for example, hydrogen, (1–4C)alkyl, halogeno, halogeno(1–4C)alkyl, nitro, (1–4C)alkanoylamino, (1–4C)alkoxy, phenyl (1–4C)alkoxy, hydroxy, carboxy, (1–4C)alkoxycarbonyl, (1–4C)alkyl bearing an amino, hydroxy, N-(1–4C)alkylamino or N,N-di(1–4C)alkylamino group, and a group —NRaRb in which Ra and Rb are independently selected from hydrogen, (1–6C)alkyl and phenyl(1–4C)alkyl, particularly (1–4C)alkanoylamino or a group —NRaRb in which Ra and Rb are independently selected from hydrogen and (1–4C)alkyl.

A combination of values for $A^1$, $A^2$ and $A^3$ which is of particular interest includes, for example, when one or two of $A^1$, $A^2$ and $A^3$ are hydrogen, and the remainder of $A^1$, $A^2$ and $A^3$ have any of the values defined above.

A preferred value for $(A^1)(A^2)(A^3)Q$ includes, for example, a 5-substituted naphth-1-yl group in which the 5-substituent is (1–4C)alkanoylamino or a group —NRaRb in which Ra and Rb are independently selected from hydrogen, methyl and ethyl. A preferred value for $(A^1)(A^2)(A^3)Q$ includes, for example, 5-N,N-di(1–4C)alkylaminonaphth-1-yl (such as 5-dimethylaminonaphth-1-yl), 5-N-(1–4C)alkylaminonaphth-1-yl (such as 5-methylaminonaphth-1-yl or 5-ethylaminonaphth-1-yl) and 5-(1–4C)alkanoylaminonaphth-1-yl (such as 5-acetamidonaphth-1-yl).

A particular group of compounds of the formula I includes, for example, compounds in which Q is naphthyl attached to the sulphonamide linkage at the 1- or 2-position of the naphthyl ring and $A^1$, $A^2$, $A^3$, $R^1$, $R^2$, W, X, Y and Z have any of the values defined above.

A further particular group of compounds of the invention includes, for example, compounds of formula Ia, or a pharmaceutically acceptable salt thereof, in which $A^4$ and $A^5$ are independently selected from any of the meanings defined hereinbefore for $A^1$, $A^2$ or $A^3$; n and m are independently selected from zero, 1, 2 or 3, provided the sum of n+m is zero, 1, 2 or 3; Ry has any of the meanings defined hereinbefore for $R^1$; and $W^1$, $X^1$, $Y^1$ and $Z^1$ have any of the meanings defined hereinbefore for W, X, Y and Z respectively. A sub-group of compounds of formula Ia includes, for example, compounds in which m=zero and n=1 or 2. A further sub-group of compounds of the formula Ia includes, for example, compounds in which m=zero, n=1 and $A^4$ is attached at the 5-position of the naphthyl ring. A further sub-group of compounds of formula Ia includes, for example, those compounds in which the naphthyl group is attached to the sulphonamido moiety at the 1-position of the naphthyl ring. Vithin these groups, compounds in which $A^4$ is, for example, the group —NRaRb in which Ra and Rb have any of the meanings defined hereinbefore (such as dialkylamino, for example dimethylamino, or alkylamino, for example ethylamino) are preferred. It will be appreciated that when there is more than one $A^4$ present, the values for each $A^4$ may be the same or different. The same applies to $A^5$ when there is more than one $A^5$ present.

Groups of compounds of the invention of particular interest include, for example, compounds of the formula Ia wherein m=0; n=1; $A^4$ is attached at the 5-position of the naphthyl ring, which ring is attached to the sulphonamido moiety at the 1-position, and $A^4$ is selected from (i) (1–4C)alkanoylamino (such as acetylamino);
(ii) the group —NRaRb in which Ra and Rb are the same and are selected from methyl, ethyl and propyl (especially methyl);
(iii) the group —NRaRb in which one of Ra and Rb is methyl and the other is ethyl or propyl; and (iv) the group —NRaRb in which one of Ra and Rb is hydrogen and the other is methyl, ethyl, propyl, isopropyl, isobutyl and sec-butyl (especially ethyl and isopropyl); and $W^1$, $X^1$, $Y^1$ and Z have any of the meanings defined hereinbefore for W, X, Y and Z respectively. Within these groups, preferred individual sub-groups of compounds include, for example, compounds in which:

(1) $W^1$ and $Z^1$ are both nitrogen; $X^1$ and $Y^1$ are both CH; and Ry is halogeno;

(2) $W^1$ and $X^1$ are both nitrogen; $Y^1$ and $Z^1$ are both $CR^2$ in which $R^2$ is hydrogen or methyl; Ry is halogeno, ethynyl, methoxy, ethoxy, methylthio or methyl (and especially when $Y^1$ is CH);

(3) $X^1$ and $Y^1$ are both nitrogen; $W^1$ and $Z^1$ are both $CR^2$ in which $R^2$ is hydrogen, methoxy or methylthio; and Ry is halogeno or methoxy (and especially when $W^1$ is CH);

(4) $X^1$ and $Z^1$ are both nitrogen; $W^1$ and $Y^1$ are both $CR^2$ in which $R^2$ is hydrogen, halogeno, methoxy, ethoxy, methyl, ethyl, methylthio or dimethylamino; and Ry is halogeno or methyl (and especially when $Y^1$ is CH); and (5) $X^1$ is nitrogen; $W^1$, $Y^1$ and $Z^1$ are all $CR^2$ in which $R^2$ is hydrogen or methoxy; and Ry is halogeno (and especially when $Y^1$ and $Z^1$ are both CH);

A further particular group of compounds of the invention includes, for example, compounds of formula Ib, or a pharmaceutically acceptable salt thereof, in which $A^6$ and $A^7$ are independently selected from any of the values defined hereinbefore for a value of $A^1$, $A^2$ or $A^3$; p and q are independently selected from zero, 1, 2 or 3, provided the sum of p+q is zero, 1, 2 or 3; Rz has any of the meanings defined hereinbefore for $R^1$; and $W^2$, $X^2$, $Y^2$ and $Z^2$ have any of the meanings defined hereinbefore for W, X, Y and Z respectively. A particular sub-group of compounds of formula Ib includes, for example, those compounds in which p=zero and q=1 or 2, especially those compounds in which p=0; q=1 and $A^7$ is attached at the para position of the phenyl ring and is selected from hydrogen and (1–4C)alkyl, such as methyl, ethyl, propyl, isopropyl, isobutyl or sec-butyl (especially isobutyl). It will be appreciated that when there is more than one $A^6$ present, the values for each $A^6$ may be the same or different. The same applies to $A^7$ when there is more than one $A^7$ present. Particular values of $A^7$ of interest include, hydrogen, (1–4C)alkyl (especially methyl and isobutyl), (1–4C)alkoxy (especially methoxy), halogeno, amino and nitro, especially when attached at the para position (when q is 1) or at the meta and para positions (when q is 2) of the phenyl ring. A further particular sub-group of compounds of formula Ib includes, for example, those compounds in which $W^2$ and $Y^2$ are both $CR^2$ and $X^2$ and $Z^2$ are both nitrogen.

Further groups of compounds of the invention may be obtained by combining any of the abovementioned particular or generic values for Q, $A^1$, $A^2$, $A^3$, $R^1$, $R^2$, W, X, Y and Z.

Compounds of the invention which are of particular interest include, for example, the specific embodiments set out hereinafter in the accompanying Examples. Of these, the compounds of formula I disclosed in Examples 1, 2, 3, 4, 10, 11, 13, 15, 18, 19, 21, 23, 24, 28, 30, 31, 34, 39, 46, 49, 50, 51, 52, 53, 54, 55, 58, 59, 61, 62, 63, 64, 65, 66 and 67 are of special interest and these compounds, or a pharmaceutically-acceptable salt thereof, are provided as a further feature of the invention.

Suitable pharmaceutically-acceptable salts include, for example, salts with alkali metal (such as sodium, potassium or lithium), alkaline earth metals (such as calcium or magnesium), ammonium salts, and salts with organic bases affording physiologically acceptable cations, such as salts with methylamine, dimethylamine, trimethylamine, piperidine and morpholine. In addition, for those compounds which are sufficiently basic suitable pharmaceutically-acceptable salts include, pharmaceutically-acceptable acid-addition salts with hydrogen halides, sulphuric acid, phosphoric acid and with organic acids such as citric acid, maleic acid, methanesulphonic acid and p-toluenesulphonic acid. Alternatively, the compound of formula I may exist in a zwitterionic form.

The compounds of formula I may be obtained by standard procedures of organic chemistry well known in the art for the production of structurally analogous compounds. Such procedures are provided as a further feature of the invention and include, by way of example, the following procedures in which the generic radicals have any of the values given above, unless stated otherwise.

(a) an amine (or an alkali metal salt thereof) of the formula II is reacted with a sulphonyl halide of formula III in which Hal. is a halogeno group (for example, chloro, bromo or iodo), in a suitable solvent.

A suitable solvent includes, for example, pyridine. A catalyst, such as 4-dimethylaminopyridine or 4-pyrrolidinopyridine, may be added to assist the coupling reaction. The reaction is generally carried out at a temperature in the range of, for example, 0° C. to 120° C. and more generally 20° C. to 120° C. Alternatively a solvent such as dichloromethane, chloroform, dimethoxyethane, tetrahydrofuran or dioxan may be used in the presence of a suitable inorganic base, such as sodium or potassium carbonate (which may be present as an aqueous solution) or an organic base, for example a teriary amine such as pyridine or triethylamine. When the alkali metal salt of the amine of formula II is used, this may be formed, for example with the use of a suitable base such as lithium diisopropylamide at a temperature, for example, about –60° C., or sodium hydride, for example, at ambient temperature, prior to the addition of the sulphonyl halide. However it will be appreciated that the reaction of a sulphonyl halide with an amine to form a sulphonamide (and the type of solvents and conditions used therein) is well-known in the art.

Alternatively an amine (or alkali metal salt thereof) of the formula II may be reacted with a sulphonate of the formula IIIa in which Re is an electron deficient phenyl group, for example a phenyl group bearing one or more electron withdrawing groups, such as nitro or cyano, in a suitable solvent. A preferred value for Re includes, for example, 4-nitrophenyl. The reaction is carried out under similar conditions to those described above.

(b) for compounds of the formula I in which W and/or Z is nitrogen, a compound of the formula IV in which L is a suitable leaving group (such as chloro, bromo, iodo, methanesulphonyloxy or p-toluenesulphonyloxy) is reacted with a sulphonamide of the formula V. The reaction is generally carried out in the presence of a base, such as an alkali metal alkoxide (such as sodium methoxide, potassium methoxide, sodium ethoxide or potassium ethoxide) or an alkali metal hydride (such as sodium or potassium hydride), or an organic base such as diisopropylethylamine. The reaction may also be carried out using a pre-formed alkali metal salt of a compound of the formula V. A suitable inert organic solvent is usually employed, for example, N,N-dimethylformamide or N-methylpyrrolidone. The reaction is generally carried out at a temperature in the range of, for example, 20° C. to 120° C.

Sulphonyl halides of formula III are well known in the art or may be obtained, for example, by the procedures described in European patent application, publication no. 558258 and 569193, or by analogy therewith. They may also be obtained by reaction of a compound $(A^1)(A^2)(A^3)Q.NH_2$ with sodium nitrite and hydrochloric acid to form a diazonium salt, followed by reaction of the diazonium salt with sulphur dioxide in dioxan and work-up with a haloacid. Compounds of the formula IIIa may be obtained from the corresponding sulphonyl chloride by reaction with the appropriate phenol (Re.OH) using conventional procedures, for example, by heating in pyridine. Compounds of formula II and IV are commercially available or are also well-known in the art, being described in standard works of heterocyclic chemistry such as those edited by Elderfield or Viessberger, and others can be obtained by analogy therewith using standard procedures of organic chemistry. The sulphonamides of formula V may be obtained from corresponding compounds of formula III using standard procedures.

(c) for a compound of the formula I in which Q is biphenyl, a compound of the formula VI in which T is a bromo, iodo or trifluoromethanesulphonyloxy group and the phenyl ring bearing T is optionally substituted is reacted with an optionally substituted phenylboronic acid (or an anhydride or ester thereof) in the presence of a suitable base and in the presence of a palladium (O), palladium(II), nickel(O) or nickel(II) catalyst. It will be appreciated that the optional substituents on the ring bearing T and those on the phenyl boronic acid are selected from any of the values for $A^1$, $A^2$ and $A^3$ defined hereinbefore, but that the sum of the number of substituents on the two rings can be no greater than three.

A preferred value for T is bromo or iodo.

Suitable catalysts include, for example, tetrakis (triphenylphosphine)-nickel(O), bis(triphenylphosphine) nickel(II)chloride, nickel(II)chloride, bis (triphenylphosphine)palladium(II)chloride, tetrakis (triphenylphosphine)palladium(O) and palladium(II) chloride, particularly the latter two catalysts and especially palladium(II)chloride.

A suitable base for use in the reaction is, for example, an alkali metal alkoxide such as sodium methoxide or sodium ethoxide, an alkali metal hydroxide such as sodium or potassium hydroxide, an alkali metal carbonate such as sodium or potassium carbonate, or an organic base such as a tri(1–6C)alkylamine, for example, triethylamine. A preferred base is an alkali metal carbonate, triethylamine or a mixture thereof.

The reaction may also be carried out in the presence of a suitable radical initiator, for example, azo (bisisobutyronitrile).

The process is generally performed in the presence of a suitable solvent or diluent, for example, a hydrocarbon, such as toluene or xylene, an ether, such as dioxan or tetrahydrofuran, an (1–4C)alcohol such as methanol, ethanol or butanol, water, or mixtures thereof.

The reaction is generally performed at a temperature in the range, for example, 50–150° C., and conveniently at or about the reflux temperature of the solvent or mixture of solvents used.

Whereafter, a compound of the formula I may be converted into another compound of the formula I by conventional functional group interconversion. For example:

(i) when an alkylamino group on Q is required, an alkanoylamino group on Q is reacted with a suitable reducing agent (for example an ethylamino group on Q may be obtained from the corresponding acetamido group by reduction with diborane or lithium aluminium hydride in tetrahydrofuran at a temperature in the general range 0° C. to 25° C.) or an amino group on Q is reductively alkylated (for example, an isopropylamino group on Q may be obtained from the corresponding amine by reaction with acetone and sodium cyanoborohydride at a temperature in the general range of 0° C. to 25° C.);

(ii) when an amino group on Q is required, a corresponding alkanoylamino group may be hydrolysed by reaction with a strong acid or base in a suitable solvent such as a (1–4C)alkanol at a temperature in the general range of 35 to 80° C., or a corresponding nitro group may be reduced using a suitable reducing agent, for example by hydrogenolysis using hydrogen in the presence of a suitable catalyst, such as palladium on charcoal in a suitable solvent or diluent such as a (1–4C)alkanol (typically methanol or ethanol or aqueous methanol or ethanol);

(iii) when a compound of the formula I is required in which X are/or Y is nitrogen, and $R_1$ is alkoxy or alkylthio, a corresponding compound of formula I in which $R^1$ is halogeno (for example chloro, bromo or iodo) may be reacted with an alkali metal alkoxide or thioalkoxide in a suitable solvent or diluent, for example N-methylpyrrolidone, DMF or an appropriate (1–4C)alkanol, or a mixture thereof, at a temperature in the range of 35–120° C.; and (iv) when a compound of the formula I is required in which X are/or Y is nitrogen, and $R_1$ is ethynyl, a corresponding compound of formula I in which $R^1$ is bromo or iodo may be reacted with a trialkylsilylacetylene (for example trimethylsilylacetylene) in the presence of palladium and copper catalysts, followed by removal of the trialkylsilyl protecting group, for example as described in Example 38 or 54 hereinafter.

It will be appreciated that it may be convenient or necessary to protect one or more functional groups with a suitable protecting group prior to carrying out the process of (a), (b) or (c) above, or prior to carrying out a functional group interconversion, followed by removal of the protecting group. Suitable protecting groups and procedures for their use, together with procedure for removing the protecting group, are well known in the art, for example as described in "Protective Groups in Organic Syntheses" by Theodora Greene (John Wiley and Sons Inc., 1981).

Whereafter, when a pharmaceutically-acceptable salt of a compound of formula I is required, it may be obtained, for example, by reaction with the appropriate base affording a physiologically-acceptable cation, or with the appropriate acid affording a physiologically-acceptable amine, or by any other conventional salt formation procedure.

Further, when an optically active form of a compound of formula I is required, one of the aforesaid processes may be carried out using an optically active starting material. Alternatively, the racemic form of a compound of formula I may be resolved, for example by reaction with a optically active form of a suitable organic base, for example, ephedrine, N,N,N-trimethyl(1-phenylethyl)ammonium hydroxide or 1-phenylethylamine, followed by conventional separation of the diastereoisomeric mixture of salts thus obtained, for example by fractional crystallisation from a suitable solvent, for example a (1–4C)alkanol, Thereafter the optically active form of said compound of formula I may be liberated by treatment with acid using a conventional procedure, for example using an aqueous mineral acid such as dilute hydrochloric acid.

As stated above, the compounds of formula I will have beneficial pharmacological effects in warm-blooded animals (including man) in diseases and medical conditions where elevated or abnormal levels of endothelin play a significant causative role. (References to studies supporting the implication of endothelin in various diseases or medical conditions are, for example, disclosed in International Patent Applications, Publication Nos. WO 93/21219 and WO 94/02474.) The compounds of the invention will thus be useful in the treatment of diseases or medical conditions such as hypertension, pulmonary hypertension, congestive heart failure, dyslipidaemia, atherosclerosis, restenosis, acute and chronic renal failure, ischaemic stroke, subarachnoid haemorrhage, intermittent claudication, critical limb ischaemia, asthma, and organ failure after general surgery or translantation. They may also be useful for the treatment of pre-eclampsia, premature labour, myocardial infarction, angina pectoris, dysrrhythmia, cardiogenic and endotoxin shock, diabetes mellitus, Raynaud's disease, scleroderma, Buerger's disease, systemic sclerosis, bronchitis, acute respiratory distress syndrome, liver cirrhosis, osteoporosis, Crohn's disease, ulcerative colitis, irritable bowel syndrome, urinary incontinence, migraine, glaucoma, arthritis and certain cancers.

The endothelin receptor antagonist activity of the compounds of the invention may be assessed using one or more of the following procedures:

Test A

The endothelin receptor antagonist activity of compounds of formula I may be assessed in vitro by their ability to inhibit binding of [$^{125}$I]-Endothelin-1 to its receptors. Human $ET_A$ or $ET_B$ receptors (sub-types of the endothelin receptor) were expressed in Mouse Erythroleukemic Cells (MEL cells) by using standard molecular techniques (for example, as described by Sambrook J., Fritsch E. F. & Maniatis T. (1989) Molecular Cloning: A Laboratory Manual, 2nd Edition, Cold Spring Harbor Press, U.S.A.). cDNA sequences encoding the human $ET_A$ and $ET_B$ receptor (Hosoda K. et al (1991), FEBS Lett., 287, 23–26 and Sakamoto A. et al, (1991), Biochem. Biophys Res. Comm., 178, 656–663) are subcloned into pBluescript vector followed by insertion into the MEL cell expression vector pEV as described by Needham et al (1992), Nuc. Acids Res., 20, 997–1003. The resultant expression vector was transfected into MEL cells by electroporation using procedures described by Shelton et al., (1993), Receptors and Channels, 1, 25–37. MEL cells expressing the recombinant human $ET_A$ or $ET_B$ receptor were grown in Dulbecco's Hodified Eagle's Medium (DMEM) with 10% Fetal Calf Serum (FCS), 1% glutamine, 1% penicillin/streptomycin and 2 mg/ml Gibco Geneticin (G-418) sulphate. After 3–6 days induction with 1% N,N-dimethylsuphoxide, the MEL cells were harvested for membrane preparation. Freshly prepared MEL cell pellets ($3\times10^9$ cells) were homogenised in 30 ml of buffer containing 50 mM 2-amino-2-(hydroxymethyl)-1,3-propanediol hydrochloride (Tris HCl), 0.19M sucrose, 5 µg/ml soybean trypsin inhibitor, 100 µg/ml bacitracin, 1 mH benzamidine and 1 mM phenanthroline pH 7.4 at 5° C. Unbroken cells and nuclei were sedimented by centrifuging the homogenate at 1500×g for 15 minutes at 5° C. The membrane pellet was resuspended in buffer and stored in liquid nitrogen until use.

[$^{125}$I]-Endothelin-1 binding to MEL cell membranes was measured in incubation buffer containing 50 mM Tris HCl, 1 mM $CaCl_2$, 0.05% polyoxyethylenesorbitan monolaurate, 0.1% Bovine Serum Albumin (BSA), 0.02% sodium azide pH 7.4 at 30° C. after 180 minutes incubation. Membrane suspension (equivalent to 1.5 µg and 0.5 µg protein/tube $ET_A$ and $ET_B$ receptor respectively) was added to the incubation containing test compound and 30 pM[$^{125}$I]-Endothelin-1 in a total volume of 225 µl. Nonspecific binding was measured in the presence of 100 nM unlabelled Endothelin-1. The incubation was terminated by harvesting the incubation with 50 mM Tris pH 7.4 through a GF/B filter on a Brandel cell harvester. The filter discs were punched out and counted in a gamma counter. Compounds are tested in triplicate over a range of concentrations and $IC_{50}$ (or $pIC_{50}$) values calculated.

In general, compounds of formula I as defined above show inhibition in Test A at a concentration of about 10 micromolar or much less.

Test B

The endothelin receptor antagonist activity of compounds of formula I may be assessed in vitro in isolated tissues by their ability to inhibit the relaxant response to endothelin-1 in the guinea-pig isolated taenia coli. Guinea pigs of either sex and weight >250 g are killed by cervical dislocation and the caecum removed and placed in cold oxygenated Krebs solution. Strips of *Taenia coli* are dissected out and approximately 4 cm lengths set up for isotonic recording in a 20 ml organ bath containing oxygenated Krebs solution at 32° C. After a 90–120 minute equilibration period to allow the tissue to spontaneously develop an increased tone, a cumulative concentration-response curve (relaxation) is constructed to endothelin-1 (0.3–10 nM). The tissue is then washed for a period of at least 90 minutes before construction of a second concentration-response curve to endothelin-1 in the presence of the test compound. The test compound is added to the organ bath (at an initial concentration of 20 µM) at least 30 minutes before constructing the second concentration-response curve to endothelin-1. The endothelin-1 concentration ratio for each experiment is determined by comparing the most parallel portions of the control and drug treated concentration-response curves. From this a $pA_2$ is calculated: $pA_2=-\log[\text{molar drug concentration}]+\log[\text{concentration ratio}-1]$.

Test C

This in vivo test involves the measurement of the antagonist effect of the test compound against the pressor response induced by intravenously-administered proendothelin-1 in a pithed rat preparation.

Male rats (280–330 g) are anaesthetised with halothane and artifically respired through a tracheal cannula. Rats are pithed by passing a 2 mm diameter needle through the orbit, through the foramen magnum, and down into the spinal canal. The left femoral vein and the right carotid artery are isolated and catheters filled with heparinised saline are implanted for administration of compounds and measurement of blood pressure respectively. Body temperature is maintained at 38° C. (as measured rectally) by a heated pad. Rats with an initial baseline mean arterial pressure of less than 55 mmHg or greater than 70 mmHg are excluded. Blood pressure is allowed to stabilize for approximately 10 minutes before a baseline reading is taken. Two initial challenges of proendothelin-1 (0.3 and 1.0 nmol kg$^{-1}$) are administered intravenously in a cumulative fashion and pressor responses recorded. Thereafter, a 55 minute recovery period is allowed and rats in which the blood pressure fails to return to within 20% of the baseline are excluded. Test compound is dosed intravenously at a dose volume of 1.0 ml kg$^{-1}$ body weight and further challenges of proendothelin-1 are administered 5 minutes later. Proendothelin-1 is administered cumulatively in increasing doses (starting at 0.3 nmolkg$^{-1}$) until pressor responses are observed. Endothelin receptor antagonism is quantified by calculating dose ratio shifts at the 30 mmHg change level.

Test D

This in vivo test involves the measurement of the antagonist effect of the test compound against the pressor response induced by intravenously-administered proendothelin-1 in a conscious rat preparation.

Male rats (260–290 g) are anaesthetised with Saffan administered via the tail vein. The right jugular vein and carotid artery are isolated and catheters filled with heparin implanted. These are exteriorised at the back of the neck using a metal trochar and the neck incision closed with autoclips. Rats are housed individually with free access to food and water during the recovery phase. Later in the day, food is removed and the rats are fasted overnight with free access to water. The following day the rats are placed in perspex restraining tubes and the arterial catheter drained and connected to a pressure transducer for measurement of mean arterial pressure. Following a ten minute stabilization period, proendothelin-1 (usually 0.3–1.0 nmol $kg^{-1}$) is administered cumulatively until a pressor response of 30 mmHg is achieved. The animals are then returned to their cages and allowed to recover for 2 hours. The test compound is administered orally (by gavage) at a known time point during the recovery period. The dose response curve to proendothelin-1 is then repeated at a fixed time after the oral dose (usually 0.5 or 1.0 hours) and again at a further time point (3 or 5 hours). Endothelin receptor antagonism is quantified by calculating dose ratio shifts at the 30 mmHg change level.

By way of illustration of the endothelin receptor antagonist activity of compounds of the formula I, the compound of Example 1 gave the following results in tests A and B described above:

In test A: $pIC_{50}$ 6.7
In test B: $pA_2$ 6.8

The compounds of formula I will generally be administered for therapeutic or prophylactic purposes to varmblooded animals (including man) requiring such treatment in the form of a pharmaceutical composition, as is well known in the pharmaceutical art. According to a further feature of the invention there is provided a pharmaceutical composition comprising a compound of formula I, or a pharmaceutically acceptable salt thereof as defined above, together with a pharmaceutically acceptable diluent or carrier. Such compositions will conveniently be in a form suitable for oral administration (e.g. as a tablet, capsule, solution, suspension or emulsion) or parenteral administration (e.g. as an injectable aqueous or oily solution, or injectable emulsion).

The compounds of formula I, or a pharmaceutically acceptable salt thereof, may also be advantageously administered for therapeutic or prophylactic purposes together with another pharmacological agent known in the general art to be of value in treating one or more of the diseases or medical conditions referred to hereinabove, such as beta-adrenergic blocker (for example atenolol), a calcium channel blocker (for example nifedipine), an angiotensin converting enzyme (ACE) inhibitor (for example lisinopril), a diuretic (for example furosemide or hydrochlorothiazide), an endothelin converting enzyme (ECE) inhibitor (for example phosphoramidon), a neutral endopeptidase (NEP) inhibitor, an HMGCoA reductase inhibitor, a nitric oxide donor, an anti-oxidant, a vasodilator, a dopamine agonist, a neuroprotective agent, a steroid, a beta-agonist, an anti-coagulant, or a thrombolytic agent. It is to be understood that such combination therapy constitutes a further aspect of the invention.

In general a compound of formula I (or a pharmaceutically acceptable salt thereof as appropriate) will be administered to man so that, for example, a daily oral dose of up to 50 mg/kg body weight (and preferably of up to 10 mg/kg) or a daily parenteral dose of up to 5 mg/kg body weight (and preferably of up to 1 mg/kg) is received, given in divided doses as necessary, the precise amount of compound (or salt) administered and the route and form of administration depending on size, age and sex of the person being treated and on the particular disease or moedical condition being treated according to principles veil known in the medical arts.

In addition to their aforesaid use in therapeutic medicine in humans, the compounds of formula I are also useful in the veterinary treatment of similar conditions affecting commercially valuable warm-blooded animals, such as dogs, cats, horses and cattle. In general for such treatment, the compounds of the formula I will be administered in an analogous amount and manner to those described above for administration to humans. The compounds of formula I are also of value as pharmacological tools in the development and standardisation of test systems for the evaluation of the effects of endothelin in laboratory animals such as cats, dogs, rabbits, monkeys, rats and mice, as part of the continuing search for new and improved therapeutic agents.

The invention will now be illustrated by the following non-limiting Examples in which, unless otherwise stated:

(i) concentrations and evaporations were carried out by rotary evaporation in vacuo;

(ii) operations were carried out at room temperature, that is in the range 18–26° C.;

(iii) chromatography and flash column chromatography was performed on Merck Kieselgel 60 (Art. no. 9385) obtained from E Merck, Darmstadt, Germany;

(iv) where a silica gel Mega Bond Elut column is referred to, this means a column containing 10 g of silica of 40 micron particle size, the silica being contained in a 60 ml disposable syringe and supported by a porous disc, obtained from Varian, Harbor City, Calif., U.S.A. under the name "vega Bond Elut SI";

(iv) yields, where given, are intended for the assistance of the reader only and are not necessarily the maximum attainable by diligent process development; and (v) $^1$H NMR spectra were normally determined at 250 MHz in $d_6$-dimethylsulphoxide ($d_6$-DMSO) or $CDCl_3$ using tetramethylsilane (THS) as an internal standard, and are expressed as chemical shifts (delta values) in parts per million relative to TMS using conventional abbreviations for designation of major peaks: s, singlet; m, multiplet; t, triplet; br, broad; d, doublet; dd, doublet of doublets.

EXAMPLE 1

A solution of 5-dimethylamino-1-naphthalenesulphonyl chloride (3.98 g), 3-amino-6-chloropyridazine (1.91 g) and 4-dimethylaminopyridine (100 mg) in pyridine (25 ml) was heated at 85° C. for 18 hours. Volatile material was removed by evaporation and dichloromethane (50 ml) was added. Insoluble material was removed by filtration and the filtrate was concentrated by evaporation. The residue was purified by flash chromatography, eluting with ethyl acetate/hexane (1:1 v/v), and the resulting foam was crystallised from ether to give 5-(dimethylamino)-N-(6-chloro-3-pyridazinyl)-1-naphthalenesulphonamide (1.74 g), m.p. 153–154° C.; mass spectrum (positive chemical ionisation ((+)ve CI)): 363 $(M+H)^+$.

EXAMPLES 2–4

Using an analogous procedure to that described in Example 1, but starting from the appropriate amino heterocycle of formula II, the following compounds of formula I were obtained (in yields in the range of 7–10%):

EXAMPLE 2

5-(Dimethylamino)-N-(5-bromo-2-pyrimidinyl)-1-naphthalenesulphonamide, m.p. 197–199° C.; mass spectrum (positive fast atom bombardment (+ve FAB), dimethylsulphoxide (DMSO)/Glycerol (GLY)): 407 (M+H)$^+$; starting from 2-amino-5-bromopyrimidine;

EXAMPLE 3

5-(Dimethylamino)-N-(5-chloro-2-pyrimidinyl)-1-naphthalenesulphonamide, m.p. 190–191° C.; mass spectrum (+ve FAB, methanol/m-nitrobenzyl alcohol (NBA)): 363 (M+H)$^+$; starting from 5-chloro-2-aminopyrimidine; and

EXAMPLE 4

5-(Dimethylamino)-N-(5-bromo-2-pyrazinyl)-1-naphthalenesulphonamide, m.p. 161–163° C.; mass spectrum (+ve FAB, methanol/NBA): 407 (M+H)$^+$; starting from 2-amino-5-bromopyrazine.

EXAMPLE 5

Sodium hydride (60% dispersion in oil; 0.16 g) was added to a solution of 2-amino-3,5-dibromopyrazine (0.506 g) in N,N-dimethylformamide (30 ml). When evolution of hydrogen ceased, 5-dimethylamino-1-naphthalenesulphonyl chloride (0.54 g) was added and the solution was heated at 95° C. for 18 hours. Volatile material was removed by evaporation and water (50 ml) was added to the residue. The mixture was extracted with ethyl acetate (20 ml), and the aqueous layer was neutralised with 0.05M aqueous acetic acid (40 ml) and extracted with ethyl acetate (3×25 ml). The extracts were washed with water (20 ml) and saturated sodium chloride solution (20 ml) and dried (MgSO$_4$). Volatile material was removed by evaporation and the residue was purified by elution with dichloromethane through a silica gel mega Bond Elut column. The resulting foam was triturated with ether/hexane (1:1 v/v) to give 5-(dimethylamino)-N-(3,5-dibromo-2-pyrazinyl)-1-naphthalenesulphonamide, (0.052 g), m.p. 178° C.; mass spectrum (+ve FAB, methanol/NBA): 485 (M+H)$^+$.

EXAMPLE 6

A solution of 2-biphenylsulphonyl chloride (0.31 g), 3-amino-6-chloropyridazine (0.5 g) in pyridine (5 ml) was stirred for 18 hours. Volatile material was removed by evaporation and 1M sodium hydroxide solution (4 ml) and methanol (10 ml) were added. The reaction mixture was stirred on a steam bath for 20 minutes and, after cooling, volatile material was again removed by evaporation. The residue was dissolved in water (100 ml) and acidified with concentrated hydrochloric acid to pH 1–2 and extracted with ethyl acetate (3×50 ml). The combined extracts were dried (MgSO$_4$) and evaporated to give a solid. The solid was recrystallised twice from isopropanol to give 2-phenyl-N-(6-chloro-3-pyridazinyl)benzenesulphonamide (0.08 g), m.p. 196–198° C.; mass spectrum (+ve FAB, methanol/dichloromethane/NBA): 346 (M+H)$^+$.

EXAMPLE 7

A solution of 5-dimethylamino-1-naphthalenesulphonyl chloride (1.35 g), 5-amino-2-chloropyridine (0.64 g), pyridine (0.4 g) and 4-dimethylaminopyridine (0.02 g) in dichloromethane (20 ml) was allowed to stand for three days. The solution was divided into two equal portions and each portion was applied to a separate silica gel Mega Bond Elut column. The columns were eluted with dichloromethane and the product-containing fractions were concentrated by evaporation. The residue was triturated with ether to give 5-(dimethylamino)-N-(2-chloro-5-pyridyl)-1-naphthalenesulphonamide (0.77 g); m.p. 145–146° C.; mass spectrum (+ve FAB, methanol/NBA): 362(M+H)$^+$.

EXAMPLE 8

Using an analogous procedure to Example 7, but using a proportionate amount of 5-amino-2-bromopyridine in place of 5-amino-2-chloropyridine, there was thus obtained (in 59% yield) 5-(dimethylamino)-N-(2-bromo-5-pyridyl)-1-naphthalenesulphonamide; m.p. 164–165° C.; mass spectrum (+ve CI): 406(M)$^+$.

EXAMPLE 9

A solution of 5-dimethylamino-1-naphthalenesulphonyl chloride (0.27 g), 2-amino-6,7-dihydro-5H-cyclopentapyrimidine (0.135 g), pyridine (0.097 ml) and 4-(dimethylamino)pyridine (0.005 g) in dichloromethane (5 ml) was stirred for 16 hours. Volatile material was removed by evaporation and the residue was purified by gradient elution with ethyl acetate/hexane through a silica gel Mega Bond Elut column. There was thus obtained 5-(dimethylamino)-N-(6,7-dihydro-5H-cyclopentapyrimidin-2-yl)-1-naphthalenesulphonamide (0.033 g), m.p. 227–230° C.; mass spectrum (+ve CI): 368 (M+H)$^+$.

The starting material 2-amino-6,7-dihydro-5H-cyclopentapyrimidine was obtained by the procedure described in *J. Am. Chem. Soc.*, 1959, 81, 3108–114.

EXAMPLE 10

3-Amino-6-iodopyridazine hydriodide (7.5 g) was suspended in water (20 ml) and 10M sodium hydroxide solution (6.5 ml) was added. The mixture was stirred for ten minutes and the solid collected by filtration and dried to give a white solid (4.4 g). The solid was dissolved in pyridine (15 ml) and 5-dimethylamino-1-naphthalenesulphonyl chloride (5.3 g) was added. The mixture was stirred for 18 hours and volatile material was removed by evaporation. The residue was recrystallised from methanol to give 5-(dimethylamino)-N-(6-iodo-3-pyridazinyl)-1-naphthalenesulphonamide (5.6 g), m.p. 176–178° C.; mass spectrum ((+)ve CI): 455 (M+H)$^+$.

EXAMPLE 11

Sodium hydride (60% dispersion in mineral oil; 0.1 g) was added portionwise to a stirred solution of 2-amino-5-bromo-3-methyl-pyrazine (0.188 g) in 1,2-dimethoxyethane (DME; 4 ml). After 5 minutes 5-dimethylamino-1-naphthalenesulphonyl chloride (0.3 g) was added, in a single portion, and the reaction was allowed to a stir for 18 hours. 2M Aqueous citric acid solution (10 ml) was added and the reaction was extracted with dichloromethane (3×25 ml). The combined extracts were dried (MgSO$_4$) and evaporated to give a brown oil. The oil was purified by chromatography on silica gel, eluting with dichloromethane/diethyl ether (1:1) to give 5-dimethylanino-N-(5-bromo-3-methyl-2-pyrazinyl)-1-naphthalenesulphonamide as a cream solid (0.138 g, 33%), m.p. 171–172° C.; mass spectrum (+ve FAB, DMSO/methanol/NBA): 421 (M+H)$^+$.

The starting material 2-amino-5-bromo-3-methylpyrazine was obtained as follows:

(i) Gaseous chlorine was passed into carbon tetrachloride (67 ml) for 30 minutes. The resulting yellow solution was added dropwise, over 30 minutes, to a stirred solution of pyridine (4.8 ml) and 2-methylpyrazine (5 g) in carbon tetrachloride (125 ml). The reaction was purged with nitrogen and volatile material was removed by evaporation. The resultant brown oil was purified by chromatography on silica gel, eluting with dichloromethane, to give 2-chloro-3-methylpyrazine as a brown oil (3.62 g, 53%); $^1$H NMR ($d_6$-DMSO): 6.59 (s,2H), 7.67 (d,1H), 7.94(d,1H); mass spectrum (+ve CI): 129 (M+H)$^+$.

(ii) 2-Chloro-3-methylpyrazine (8 g) was heated in a sealed glass tube with aqueous ammonia (d=0.88;50 ml) at 200° C. for 96 hours. After cooling, 2H aqueous potassium hydroxide solution (25 ml) was added and the reaction mixture was extracted with diethyl ether (6×150 ml). The combined extracts were dried ($MgSO_4$) and evaporated to give a yellow oil. The oil was purified by chromatography on silica gel, eluting with dichloromethane/diethyl ether (1:1), to give 2-amino-3-methylpyrazine as a white solid (2.8 g, 41%), m.p. 136–138° C.; mass spectrum (+ve CI): 110 (M+H)$^+$.

(iii) A solution of bromine (0.26 ml) in chloroform (40 ml) was added dropwise to a stirred solution of 2-amino-3-methylpyrazine (0.453 g) and pyridine (0.4 ml) in chloroform (100 ml) with shielding from sunlight, over a period of 1 hour. The reaction mixture was stirred for a further 30 minutes and then water (25 ml) was added. The organic layer was separated, dried ($MgSO_4$) and evaporated to afford a brown oil. The oil was purified by chromatography on silica gel, eluting with dichloromethane, to give 2-amino-5-bromo-3-methylpyrazine as a white solid (0.312 g, 28%), m.p. 51–52°° C.; mass spectrum (+ve CI): 188 (M+H)$^+$.

EXAMPLE 12

Using an analogous procedure to that described in Example 11, but using a proportionate amount of 2-amino-5-bromo-3-ethylpyrazine, there was thus obtained 5-dimethylamino-N-(5-bromo-3-ethyl-2-pyrazinyl)-1-naphthalenesulphonamide, m.p. 171–172° C., mass spectrum (+ve FAB, DMSO/methanol/NBA): 435 (M+H)$^+$.

The starting material 2-amino-5-bromo-3-ethylpyrazine was obtained as follows:

(i) Ethyl 2-bromopropionate (91.5 ml) was added to aqueous ammonia (d=0.88, 650 ml) at 0° C., giving a biphasic system. Liquid ammonia (50 ml) was added and the clear solution stirred at 0° C. for 5 hours and then at ambient temperature for 18 hours. Volatile material was removed by evaporation to give 2-aminobutanamide hydrobromide as a white crystalline solid, (113.5 g), m.p. 152–154° C.; mass spectrum (+ve CI): 103 (M+H)$^+$.

(ii) Aqueous glyoxal (50 ml), was added over one minute to a stirred solution of 2-aminobutanamide hydrobromide (61.9 g), in aqueous methanol (650 ml methanol, 70 ml water) at −40° C. 10.8M Aqueous sodium hydroxide solution (76.6 ml) was then added over one hour, keeping the temperature at −40° C. The reaction was then allowed to warm to ambient temperature over 18 hours and concentrated hydrochloric acid (41 ml) was added, followed by solid sodium hydrogen carbonate (33 g). The reaction mixture was filtered and the filtrate concentrated to a volume of approximately 100 ml. The concentrated solution was extracted with dichioromethane (3×250 ml), and the combined organic extracts were dried ($MgSO_4$). Solvent was removed by evaporation to give 3-ethyl-2-hydroxypyrazine as a yellow solid, (30.3 g, 74%); $^1$H NHR ($d_6$-DMSO, 200 MHz): 1.15 (t,3H), 2.67 (q,2H), 7.15–7.25 (m,2H), 12.00 (s,1H); mass spectrum (+ve CI): 125 (M+H)$^+$.

(iii) 3-Ethyl-2-hydroxypyrazine (5 g) was heated with phosphorus oxychloride (15 ml) at reflux for 3 hours. The reaction was allowed to cool to ambient temperature and then poured onto 200 g of crushed ice. The mixture was extracted with dichloromethane (3×150 ml) and the combined extracts were dried ($MgSO_4$). Volatile material was removed by evaporation to give a brown oil. The oil was purified by chromatography on silica gel, eluting with dichoromethane, to give 2-chloro-3-ethylpyrazine as a colourless oil (5.64 g, 98%); $^1$H MNR ($d_6$-DMSO, 200 MHz): 1.25 (t,3H), 2.93 (q,2H), 8.36 (d,1H), 8.59 (d,1H); mass spectrum (+ve CI): 143 (M+H)$^+$.

(iv) Using an analogous procedure to that described in Example 11, part (ii), but using a proportionate amount of 2-chloro-3-ethylpyrazine, there was thus obtained 2-amino-3-ethylpyrazine; $^1$H NMR ($d_6$-DMSO): 1.17 (t, 3H), 2.59 (q, 2H), 6.10 (s,2H), 7.64 (d, 1H), 7.74 (d, 1H); mass spectrum (+ve CI): 124 (M+H)$^+$.

(v) Using an analogous procedure to that d escribed in Example 11, part (iii), but using a proportionate amount of 2-chloro-3-ethylpyrazine, there was thus obtained 2-amino-5-bromo-3-ethylethylpyrazine, m.p. 68–69° C.; mass spectrum (positive electron impact (+ve EI)): 201 (M+H)$^+$.

EXAMPLE 13

Using an analogous procedure to that described in Example 11, but using a proportionate amount of 2-amino-5-chloropyrazine, there was thus obtained 5-dimethylamino-N-(5-chloro-2-pyrazinyl)-1-naphthalenesulphonamide, m.p. 112–113° C.; $^1$H NMR ($d_6$-DMSO): 2.7 (s,6H), 7.3 (d,1H), 7.6 (m,2H), 8.1 (s,1H), 8.3 (s,1H), 8.3 (m,2H), 8.5 (d,1H), 12.1 (s,1H); mass spectrum (+ve CI): 363 (M+H)$^+$.

The starting material 2-amino-5-chloropyrazine was obtained using an analogous procedure to that described in Example 11, part (i), but using a proportionate amount of 2-aminopyrazine; $^1$H NMR ($d_6$-DMSO): 6.6 (br,2H), 7.7 (d,1H), 7.9 (d,1H); mass spectrum (+ve CI): 130 (M+H)$^+$.

EXAMPLE 14

Using an analogous procedure to that described in Example 11, but using a proportionate amount of 2-amino-3,5-dichloropyrazine, there was thus obtained 5-dimethylamino-N-(3,5-dichloro-2-pyrazinyl)-1-naphthalenesulphonamide, m.p. 144–145° C.; mass spectrum (+ve CI); 397 (M+H)$^+$.

The starting material 2-amino-3,5-dichloropyrazine was obtained using an analogous procedure to that described in Example 11, part (i), but using a proportionate amount of 2-aminopyrazine and twice the volume of chlorine in carbon tetrachloride; m.p. 117–118° C.; mass spectrum (+ve CI): 164 (M+H)$^+$.

EXAMPLE 15

Using an analogous procedure to that described in Example 9, but using a proportionate amount of 2-amino-3,5-dimethylpyrazine, there was thus obtained 5-dimethylamino-N-(3,5-dimethyl-2-pyrazinyl)-1-naphthalenesulphonamide, m.p. 86–88° C.; $^1$H NHR ($d_6$-DMSO, 200 MHz): 2.3 (s,3H), 2.4 (s,3H), 2.9 (s,6H), 7.3 (d,1H), 7.6 (d,1H), 7.7 (d,1H), 7.8 (s,1H), 8.3 (d,1H), 8.4 (d,1H), 1.5 (d,1H), 10.8 (s,1H); mass spectrum (+ve CI): 357 (M+H)$^+$.

EXAMPLE 16

Using an analogous procedure to that described in Example 11, but using a proportionate amount of 2-amino-5-methylpyrazine, there was thus obtained 5-dimethylamino-N-(5-methyl-2-pyrazinyl)-1-naphthalenesulphonamide, m.p. 153–54° C.; mass spectrum (+ve FAB, DMSO/NBA): 343 (M+H)$^+$.

EXAMPLE 17

Using an analogous procedure to that described in Example 11, but using a proportionate amount of 2-amino-3-bromo-5-methylpyrazine, there was thus obtained 5-dimethylamino-N-(3-brozo-5-methyl-2-pyrazinyl)-1-naphthalenesulphonamide, m.p. 174–175° C.; mass spectrum (+ve FAB, DMSO/NBA): 421 (M+H)$^{30}$.

The starting material 2-amino-3-bromo-5-methylpyrazine was obtained using an analogous procedure to that described in Example 11, part (iii), but using a proportionate amount of 2-amino-5-methylpyrazine, m.p. 51–52° C.; mass spectrum (+ve CI): 188 (M+H)$^+$.

EXAMPLE 18

Using an analogous procedure to that described in Example 11, but using a proportionate amount of 2-amino-3-methoxy-5-methylpyrazine, there was thus obtained 5-dimethylamino-N-(3-methoxy-5-methyl-2-pyrazinyl)-1-naphthalenesulphonamide, m.p. 126–127° C.; $^1$H NMR (d$_6$-DMSO): 2.23 (s,3H), 2.84 (s,6H), 3.95 (s,3H), 7.24 (d,1H), 7.52 (s,1H), 7.58 (t,1H), 7.66 (t,1H), 8.28 (d,1H), 8.46 (t,2H); mass spectrum (+ve FAB, methanol/NBA): 373 (M+H)$^+$.

The starting material 2-amino-3-methoxy-5-methylpyrazine was obtained as follows:

(i) 2-Amino-3-bromo-5-methylpyrazine (0.374 g) was added to a freshly prepared solution of sodium methoxide in methanol (made by addition of sodium (0.115 g) to methanol (6 ml)). The reaction was heated under reflux for 18 hours, cooled to ambient temperature and the solvent removed by evaporation. Water (5 ml) was added to the residue and extracted with dichloromethane (3×20 ml). The combined organic extracts were dried (MgSO$_4$) and the solvent removed by evaporation. The residue was purified by chromatography on silica gel, eluting with dichloromethane to give 2-amino-3-methoxy-5-methylpyrazine as a white crystalline solid (0.208 g, 75%), m.p. 67–69° C.; mass spectrum (+ve CI): 140 (M+H)$^+$.

EXAMPLE 19

Using an analogous procedure to that described in Example 11, but using a proportionate amount of 2-amino-5-chloro-3-methoxypyrazine, there was thus obtained 5-dimethylamino-N-(5-chloro-3-methoxy-2-pyrazinyl)-1-naphthalenesulphonamide, m.p. 137–138° C.; $^1$H NMR (d$_6$-DMSO): 2.83 (s,6H), 3.91 (s,3H), 7.25 (d,1H), 7.63 (m,2H), 7.75 (s,1H), 8.31 (dd,1H), 8.43 (d,1H), 8.49 (d,1H), 11.49 (s,1H); mass spectrum (+ve FAB): 393 (M+H)$^+$.

The starting material 2-amino-5-chloro-3-methoxypyrazine was obtained using an analogous procedure to that described in Example 18, part (i), but using a proportionate amount of 2-amino-3,5-dichloropyrazine; mass spectrum (+ve CI): 160 (M+H)$^+$.

EXAMPLE 20

Using an analogous procedure to that described in Example 11, but using a proportionate amount of 2-amino-3-bromo-5-chloropyrazine, there was thus obtained 5-dimethylamino-N-(3-bromo-5-chloro-2-pyrazinyl)-1-naphthalenesulphonamide, m.p. 80–85° C.; $^1$H NMR (d$_6$-DMSO): 2.8 (s,6H), 7.3 (d,1H), 7.6 (t,1H), 7.63 (t,1H), 8.25 (s,1H), 8.28 (d,1H), 8.45 (d,1H), 8.48 (d,1H); mass spectrum (+ve FAB, methanol/NBA): 441 (M+H)$^+$.

The starting material 2-amino-3-bromo-5-chloropyrazine was obtained using an analogous procedure to that described in Example 11, part (iii), but using a proportionate amount of 2-amino-5-chloropyrazine; m.p. 102–105° C.; mass spectrum (+ve CI): 208 (M+H)$^+$.

EXAMPLE 21

5-Dimethylamino-1-naphthalenesulphonyl chloride (15.2 g) and 2-amino-5-bromo-3-methoxypyrazine (obtained as described in *Gazz. Chim. Ital.* 1960, 90, 1807) (9.5 g) were mixed intimately in a mortar and pestle and added to pyridine (150 ml) at 0° C. The solution was kept at 0° C. for 1 hour and then heated at 80° C. for 18 hours. Volatile material was removed by evaporation and dichloromethane (250 ml) was added to the residue. Insoluble material was removed by filtration and the filtrate was washed with water (100 ml) and saturated sodium chloride solution (100 ml). The solution was treated with charcoal and dried (MgSO$_4$). The solvent was removed by evaporation and the residue was purified by flash chromatography, eluting with ethyl acetate/hexane (1:4 v/v). The resulting solid was triturated with ether and recrystallised from ethanol to give 5-dimethylamino-N-(5-bromo-3-methoxy-2-pyrazinyl)-1-naphthalenesulphonamide (4.7 g), m.p. 166–167° C.; $^1$H NMR (d$_6$-DMSO): 2.8 (s,6H), 3.9 (s,3H), 7.2 (d,1H), 7.55–7.7 (d,2H), 7.8 (s,1H), 8.3 (d,1H), 8.4–8.5 (m,2H), 11.5 (s,1H); mass spectrum (+ve CI): 437 (M+H)$^+$.

The corresponding sodium salt was prepared as follows: 5-Dimethylamino-N-(5-bromo-3-methoxy-2-pyrazinyl)-1-naphthalenesulphonamide (9.92 g) was dissolved in methanol (300 ml) and a solution of sodium hydroxide (0.908 g) in water (25 ml) was added. The solvents were removed by evaporation and the residue was dissolved in water (250 ml) and the solution filtered. The aqueous solution was then freeze-dried to give 5-dimethylamino-N-(5-bromo-3-methoxy-2-pyrazinyl)-1-naphthalenesulphonamide sodium salt (10.4 g); microanalysis found: C, 43.2; H, 3.5; Br, 17.0; N, 11.7; Na, 4.8; S, 6.9%; C$_{17}$H$_{16}$BrN$_4$NaO$_3$S.(0.8H$_2$O) requires: C, 43.1; H, 3.7; Br, 16.9; N, 11.8; Na, 4.9; S, 6.8%; mass spectrum (+ve FAB, DMSO/methanol/GLY): 437 (M-Na+H)$^+$, 459 (M+H)$^+$.

EXAMPLES 22–25

Using an analogous procedure to that described in Example 21, but starting from the appropriate amino heterocycle of formula II, the following compounds of formula I were obtained (in yields in the range 4–55%):

EXAMPLE 22

5-Dimethylamino-N-(6-bromo-2-methoxy-3-pyridyl)-1-naphthalenesulphonamide, m.p. 107–111° C.; $^1$H NMR (d$_6$-DMSO): 2.8 (s,6H), 3.3 (s,3H), 7.1 (d,1H), 7.3 (d,1H), 7.45 (d,1H), 7.5–7.6 (m,2H), 8.0 (d,1H), 8.3 (d,1H), 8.5 (d,1H), 10.2 (s, 1H); mass spectrum (+ve EI): 435 (M$^+$); starting from 3-amino-6-bromo-2-methoxypyridine (obtained as described in *Helv Chim. Acta.*, 1964, 47, 363);

EXAMPLE 23

5-Dimethylamino-N-(6-bromo-3-pyridazinyl)-1-naphthalenesulphonamide, m.p. 151–153° C.; mass spectrum (+ve FAB, methanol/dichloromethane/NBA): 407 (M+H)$^+$; starting from 3-amino-6-bromopyridazine (obtained as described in *J. Am. Chem. Soc.*, 1954, 76, 3225);

EXAMPLE 24

5-Dimethylamino-N-(5-bromo-3-ethoxy-2-pyrazinyl)-1-naphthalenesulphonamide, m.p. 179–181° C.; mass spectrum (+ve CI): 451 (M+H)$^+$; starting from 2-amino-5-bromo-3-ethoxypyrazine, which was obtained as follows:

A solution of 2-amino-3,5-dibromopyrazine (obtained as described in *Gazz. Chim. Ital.*, 1960, 90, 1807) (1.26 g) and sodium ethoxide (0.4 g) in ethanol (50 ml) was heated under reflux for 4 hours. Volatile material was removed by evaporation and the residue was partitioned between water (20 ml) and ethyl acetate (50 ml). The organic layer was separated and dried (MgSO$_4$). Volatile material was removed by evaporation to give 2-amino-5-bromo-3-ethoxypyrazine (0.95 g); $^1$H NMR (d$_6$-DMSO): 1.4 (t, 3H), 4.3 (q, 2H), 6.4 (br s, 2H), 7.6 (s, 2H); mass spectrum (+ve CI): 218 (M+H)$^+$.

EXAMPLE 25

5-Dimethylanino-N-(5-bromo-3-methylthio-2-pyrazinyl)-1-naphthalenesulphonamide, m.p. 84° C.; mass spectrum (+ve FAB, methanol/NBA): 452 (M$^+$), 453 (M+H)$^+$; starting from 2-amino-5-bromo-3-methylthiopyrazine, which was obtained as follows:

A solution of 2-amino-3,5-dibromopyrazine (2.0 g) and sodium methylthiolate (1.12 g) in methanol (80 ml) was heated under reflux for 1 hour. Volatile material was removed by evaporation and the residue vas partitioned between water (50 ml) and ethyl acetate (100 ml). The organic layer was separated and dried (MgSO$_4$). Volatile material was removed by evaporation to give 2-amino-5-bromo-3-methylthiopyrazine (1.64 g); $^1$H NMR (d$_6$-DMSO): 2.6 (s, 3H), 6.5 (br s, 2H), 7.8 (s, 1H); mass spectrum (+ve CI): 220 (M+H)$^+$.

EXAMPLE 26

A 2M solution of lithium diisopropylamide in tetrahydrofuran (THF)/heptane (1:1 v/v; 2.3 ml) was added over 10 minutes to a stirred solution of 2-amino-5-bromo-3-dimethylaminopyrazine (0.45 g) in dry THF (25 ml) at −60° C. The solution was stirred at −60° C. for 1 hour and then 5-dimethylamino-1-naphthalenesulphonyl chloride (0.62 g) was added portionwise over 5 minutes. The solution was allowed to warm to ambient temperature and then stirred for 18 hours. Ether (20 ml) was added and the solution was extracted with water (2×20 ml). The aqueous extracts were neutralised to pH 7 with 10% citric acid solution and extracted with ethyl acetate (2×20 ml). The organic extracts were combined and dried (MgSO$_4$). Volatile material was removed by evaporation and the residue was purified by elution with ethyl acetate/hexane (1:3 v/v) through a silica gel Mega Bond Elut column. The resulting solid was further purified by elution with dichloromethane through a fresh silica gel Mega Bond Elut column to give 5-dimethylamino-N-(5-bromo-3-dimethylamino-2-pyrazinyl)-1-naphthalenesulphonamide (0.125 g), m.p. 180–182° C. (after trituration with ether); mass spectrum (+ve FAB, methanol/dichloromethane/DMSO/NBA): 450 (M+H)$^+$.

The starting 2-amino-5-bromo-3-dimethylaminopyrazine was obtained as follows:

2-Amino-3,5-dibromopyrazine (1.0 g) was dissolved in a solution of dimethylamine in ethanol (33% v/v; 20 ml) and the solution was heated under reflux for 18 hours. Volatile material was removed by evaporation and the residue was purified by elution with dichloromethane through a silica gel Mega Bond Elut column to give 2-amino-5-bromo-3-dimethylaminopyrazine (0.67 g); $^1$H NMR (d$_6$-DMSO): 2.75 (s, 6H), 6.1–6.2 (br s, 2H), 7.6 (s, 1H); mass spectrum (+ve CI): 217 (M+H)$^+$.

EXAMPLE 27

2-Amino-5-bromo-6-chloropyrazine (0.417 g) was added to a stirred suspension of sodium hydride (oil-free; 0.24 g) in dry dimethoxyethane (20 ml). When evolution of hydrogen ceased, 5-dimethylamino-1-naphthalenesulphonyl chloride (0.594 g) was added. The mixture was stirred for 24 hours and then water (25 ml) and 2M hydrochloric acid (2 ml) were added. The mixture was extracted with ethyl acetate (2×25 ml) and the extracts were dried (MgSO$_4$). Volatile material was removed by evaporation and the residue was purified by elution with ethyl acetate/hexane (1:3 v/v) through a silica gel Mega Bond Elut column to give 5-dimethylamino-N-(5-bromo-6-chloro-2-pyrazinyl)-1-naphthalenesulphonamide (0.46 g), m.p. 180–182° C. (after trituration with ether); mass spectrum (+ve FAB, methanol/NBA): 442 (M$^+$).

The starting 2-amino-5-bromo-6-chloropyrazine was obtained as follows:

A solution of 2-amino-6-chloropyrazine (5.0 g) and N-bromosuccinimide (13.9 g) in chloroform (200 ml) was heated under reflux for 2 hours. Insoluble material was removed by filtration and the filtrate was concentrated by evaporation. The residue was purified by flash chromatography on silica gel, eluting with dichloromethane, to give 2-amino-5-bromo-6-chloropyrazine (1.5 g); m.p. 120–122° C.; mass spectrum (+ve CI): 208 (M+H)$^+$.

EXAMPLES 28–29

Using an analogous procedure to that described in Example 21, but starting from 5-acetamido-1-naphthalenesulphonyl chloride (obtained as described in European Patent Application, Publication No. 0558258) and the appropriate amino heterocycle of formula II, the following compounds of formula I were obtained (in yields in the range 8–20%):

EXAMPLE 28

5-Acetamido-N-(5-brono-3-methoxy-2-pyrazinyl)-1-naphthalenesulphonamide; m.p. 221–225° C.; $^1$H NMR (d$_6$-DMSO): 2.2 (s,3H), 3.9 (s,3H), 7.55–7.75 (m,3H), 7.8 (s,1H), 8.3–8.4 (m,2H), 8.65 (d,1H), 10.05 (s,1H), 11.4–11.6 (br, 1H); mass spectrum (+ve FAB, methanol/dichloromethane/DMSO/NBA): 451 (M+H)$^+$; and

EXAMPLE 29

5-Acetamido-N-(6-chloro-3-pyridazinyl)-1-naphthalenesulphonamide; m.p. 161–162° C.; mass spectrum (+ve FAB, Methanol/NBA): 377 (M+H)$^+$.

EXAMPLE 30

A 1.0M solution of diborane in THF (6.65 ml) was added to a solution of 5-acetamido-N-(5-bromo-3-methoxy-2-pyrazinyl)-1-naphthalenesulphonamide (0.725 g) in dry THF (60 ml) at 0° C. under argon. The solution was heated under reflux for 24 hours and then volatile material was removed by evaporation. The residue was purified by flash chromatography, eluting with ethyl acetate/hexane (7:13 v/v), to give 5-ethylamino-N-(5-bromo-3-methoxy-2-pyrazinyl)-1-naphthalenesulphonamide (0.23 g), m.p. 216–218° C. (after trituration with ether); $^1$H NMR (d$_6$-DMSO): 1.3 (t,3H), 3.25 (q,2H), 3.9 (s,3H), 6.6 (d,1H), 7.4–7.6 (m,2H), 7.75 (s,1H), 7.95 (d,1H), 8.25 (d,1H), 8.5 (d,1H), 11.3–11.5 (br, 1H); mass spectrum (+ve FAB, methanol/NBA): 438 (M+H)$^+$.

EXAMPLE 31

Using an analogous procedure to that described in Example 30, but starting from 5-acetamido-N-(6-chloro-3-pyridazinyl)-1-naphthalenesulphonamide, there was thus obtained (in 19% yield) 5-ethylamino-N-(6-chloro-3-pyridazinyl)-1-naphthalenesulphonamide, m.p. 166–168° C.; mass spectrum (+ve CI): 363 (M+H)$^+$.

EXAMPLE 32

Using an analogous procedure to teat described in Example 30, but starting from 5-acetamido-N-(5-bromo-2-pyrazinyl)-1-naphthalenesulphonamide, there was thus obtained (in 15% yield) 5-ethylamino-N-(5-bromo-2-pyrazinyl)-1-naphthalenesulphonamide, m.p. 220–222° C.; mass spectrum (+ve CI): 407 (M+H)$^+$.

The starting 5-acetamido-N-(5-bromo-2-pyrazinyl)-1-naphthalenesulphonamide was obtained (in 41% yield) from 5-acetamido-1-naphthalenesulphonamide chloride and 2-amino-5-bromopyrazine using an analogous procedure to that described in Example 21; m.p. 227–229° C., mass spectrum (+ve CI): 421 (M+H)$^+$.

EXAMPLE 33

5-Dimethylamino-1-naphthalenesulphonyl chloride (0.296 g) and 5-amino-2,4-dimethoxypyrimidine (0.155 g) were mixed together as solids. Pyridine (10 mls) was added and the solution was stirred at 0° C. for 30 minutes. The mixture was then heated at 80° C. for 5 hours. Volatile material was removed by evaporation and the residue was purified by elution with dichloromethane through a silica gel Mega Bond Elut column to give 5-dimethylamino-N-(2,4-dimethoxy-5-1-naphthalenesulphonamide (0.28 g), m.p. 201° C.; $^1$H NMR (d$_6$-DMSO): 2.85 (s, 6H), 3.1 (s, 3H), 3.8 (s, 3H), 7.3 (d, 1H), 7.55 (q, 2H); 7.95 (d, 1H), 8.05 (s, 1H), 8.30 (d, 1H), 8.48 (d, 1H), 9.85 (s, 1H); mass spectrum (+ve CI): 389 (M+H)$^+$.

The starting 5-amino-2,4-dimethoxypyrimidine was obtained as follows:

(i) 2,4-Dichloro-5-nitropyrimidine (9.7 g), prepared using the procedure in *J. Chem. Soc.*, 1951, 1565, was added to a solution of sodium methoxide in methanol (obtained from sodium (2.8 g) and methanol (50 ml)) at 0–5° C. The mixture was heated at reflux for 2 hours and poured onto ice water (200 ml). The suspended solid was collected by filtration and dried under vacuum to give 2,4-dimethoxy-5-nitropyrimidine (7.6 g) as a solid, m.p. 92–93° C.

(ii) A solution of 2,4-dimethoxy-5-nitropyrimidine (7.5 g) in methanol (200 ml) was hydrogenated under an atmosphere of hydrogen, using 10% palladium on charcoal (1 g) as catalyst. After uptake of the theoretical volume of hydrogen, the catalyst was removed by filtration and the filtrate was evaporated to give a red solid. The solid was purified by elution with ethyl acetate/methanol (9:1 v/v) through a bed of silica gel to give 5-amino-2,4-dimethoxypyrimidine (5.2 g) as a buff solid, m.p. 82–84° C.; $^1$H NMR (CDCl$_3$): 3.2 (s, 2H), 3.92 (s, 3H), 4.02 (s, 3H), 7.71 (s, 1H).

EXAMPLE 34

Sodium hydride (60% dispersion in oil; 0.1 g) was added to a solution of 5-amino-2-chloro-4-methoxypyrimidine (0.159 g) in 1,2-dimethoxyethane (10 ml). When evolution of hydrogen had ceased, 5-dimethylamino-1-naphthalenesulphonyl chloride (0.336 g) was added and the solution was stirred for 2 hours. Volatile material was then removed by evaporation. The residue was purified by elution with ethyl acetate/hexane/acetic acid (0–20% ethyl acetate, 0.1% acetic acid) through a silica gel Mega Bond Elut column to give 5-dimethylamino-N-(2-chloro-4-methoxy-5-pyrimidinyl)-1-naphthalenesulphonamide (0.067 g) as an oil; $^1$H NMR (d$_6$-DMSO): 2.85 (s, 6H), 3.39 (s, 3H), 7.3 (d, 1H), 7.6 (t of t, 2H), 8.08 (d, 1H), 8.25 (s, 1H), 8.30 (d, 1H), 8.5 (d, 1H), 10.42 (s, 1H); mass spectrum (+ve FAB, dichloromethane/NBA): 393 (M+H)$^+$.

The starting material 5-amino-2-chloro-4-methoxypyrimidine was obtained as follows:

(i) A mixture of 5-amino-2,4-dichloropyrimidine (0.32 g) (obtained as described in *Chem. Pharm. Bull.*, (JAPAN), 1958, 6, 343–346) and a solution of sodium methoxide in methanol (from sodium (0.05 g) and methanol (25 ml)) was heated at reflux for 15 minutes and allowed to cool. Volatile material was removed by evaporation and a small volume of water added. The mixture was extracted twice with ether and the combined extracts were dried (MgSO$_4$) and evaporated to give 5-amino-2-chloro-4-methoxypyrimidine (0.2 g) as an oil; $^1$H NMR (d$_6$-DMSO): 3.92 (s, 3H), 5.25 (s, 2H), 7.72 (s, 1H); mass spectrum (+ve CI): 160 (M+H)$^+$.

EXAMPLE 35

Using an analogous procedure to that described in Example 34, but starting from 5-amino-2-chloro-4-methylthiopyrimidine, there was thus obtained 5-dimethylamino-N-(2-chloro-4-methylthio-5-pyrimidinyl)-1-naphthalenesulphonamide (0.263 g; 34% yield); $^1$H NMR (CDCl$_3$): 2.39 (s, 3H), 2.89 (s, 6H), 7.1–7.3 (m, 2H), 7.48 (t, 1H), 7.58 (t, 1H), 8.18 (d, 2H), 8.28 (d, 1H), 8.56 (d, 1H); mass spectrum (+ve FAB, methanol/NBA): 409 (M+H)$^+$.

The starting material 5-amino-2-chloro-4-methylthiopyrimidine was obtained as follows:

Sodium methanethiolate (0.342 g) was added to a solution of 5-amino-2,4-dichloropyrimidine (1 g) in methanol (5 ml) and the mixture was heated at reflux for 2 hours. Volatile material was then removed by evaporation and water (1 ml) was added. The suspended solid was collected by filtration, washed with hexane (10 ml) and dried under vacuum to give 5-amino-2-chloro-4-methylthiopyrimidine (0.3 g); $^1$H NMR (CDCl$_3$): 2.55 (s, 3H), 7.75 (s, 1H); mass spectrum (+ve CI): 175 (M+H)$^+$.

EXAMPLE 36

Sodium hydride (60% dispersion in oil; 0.25 g) was added to a solution of 3-amino-6-chloro-5-methylpyridazine (0.36 g) in dry 1,2-dimethoxyethane (10 ml). When evolution of gas ceased, 5-dimethylamino-1-naphthalenesulphonyl chloride (0.67 g) was added and the reaction mixture was stirred for 45 minutes. 7% aqueous citric acid solution (10 ml) was added, the organic phase was separated and the aqueous layer was extracted with ethyl acetate (2×20 ml). The combined organic phases were washed with water (10 ml) and dried (MgSO$_4$). Volatile material was removed by evaporation to give a gum which was triturated first with dichloromethane and then ether to give 5-dimethylamino-N-(6-chloro-5-methyl-3-pyridazinyl)-1-naphthalenesulphonamide (0.2 g), m.p. 110–112° C.; $^1$H NMR (d$_6$-DMSO): 2.30 (s,3H), 2.8 (s,6H), 7.23 (d,1H), 7.52–7.7 (m,3H), 8.3–8.5 (m,3H); mass spectrum (+ve FAB, methanol/dichloromethane/NBA): 376 (M)$^+$.

The starting material, 3-amino-6-chloro-5-methylpyridazine, was prepared by the procedure described in *Aust. J. Chem.*, 1986, 39, 1803.

EXAMPLE 37

Using an anlogous procedure to that described in Example 36, but starting from 3-amino-6-chloro-4-methylpyridazine, there was obtained 5-dimethylamino-N-(6-chloro-4-methyl-3-pyridazinyl)-1-naphthalenesulphonamide, m.p. 182–186° C.; $^1$H NPR (d$_6$-DMSO, 200 MHz): 2.83 (s,6H), 7.24 (d,1H), 7.53–7.73 (m,3H), 8.3–8.5 (m,3H); mass spectrum (+ve CI): 377 (M+H)$^+$.

The starting material, 3-amino-6-chloro-4-methylpyridazine, was obtained by the procedure described in *Aust.J.Chem.*, 1986, 39, 1803, by further crystallisation of the mother liquors.

EXAMPLE 38

5-Dimethylamino-N-(6-(2-trimethylsilyl-1-ethynyl)-3-pyridazinyl)-1-naphthalenesulphonamide (0.14 g) was suspended in methanol (4 ml) and a 1M solution of potassium fluoride dehydrate in methanol (1.2 ml) was added. After 15 minutes the solvent was removed by evaporation and the residue was dissolved in dichloromethane (10 ml) then washed with 7% aqueous citric acid solution (10 ml). The aqueous layer was separated and washed with dichloromethane (2×10 ml). All the organic phases were combined, washed with water (10 ml) and dried (mgSO$_4$). Solvent was removed by evaporation to give a solid which was purified by gradient elution with methanol/dichloromethane through a silica gel Mega Bond Elut column. There was thus obtained 5-dimethylanino-N-(6-ethynyl-3-pyridazinyl)-1-naphthalenesulphonamide (0.075 g), u.p. 122–124° C., decomposition; mass spectrum (+ve FAB, DMSO/NBA): 353 (M+H)$^+$.

The starting material, 5-dimethylamino-N-(6-(2-trimethylsilyl-1-ethynyl)-3-pyridazinyl)-1-naphthalenesulphonamide, was obtained as follows:

Triethylamine (0.21 ml) was added to a stirred mixture of trimethylsilylacetylene (0.42 ml), 5-(dimethylamino)-N-(6-iodo-3-pyridazinyl)-1-naphthalenesulphonamide (0.45 g), copper(I) iodide (50 mg), bis(triphenylphoshinepalladium (II) chloride (50 mg), palladium(II)acetate (50 mg) and tri-o-tolylphosphine (30 mg) in dimethylformamide (8 ml) under a nitrogen atmosphere. After stirring for 18 hours at 40° C., further aliquots of trimethylsilylacetylene (0.21 ml) and triethylamine (0.21 ml) were added and the reaction heated to 70° C. for 6 hours. On cooling, volatile material was removed by evaporation and the residue was dissolved in dichloromethane (30 ml). The solution was washed with 7% aqueous citric acid solution (20 ml), water (30 ml) and then dried (MgSO$_4$). Solvent was removed by evaporation to give an oil which was purified by gradient elution with toluene/ethyl acetate through a silica gel Mega Bond Elut column. There was thus obtained 5-(dimethylamino)-N-(6-(2-trimethylsilyl-1-ethynyl)-1-pyridazinyl)-1-naphthalenesulphonamide (0.24 g); $^1$H (d$_6$-DMSO): 0.25 (s,9H), 2.85 (s,6H), 7.13–7.32 (m,2H), 7.5–7.72 (m,5H), 8.27 (d,1H), 8.45 (t,2H); mass spectrum (+ve FAB, DMSO/NBA): 425 (M+H)$^+$.

EXAMPLE 39

5-Dimethylamino-N-(6-chloro-3-pyridazinyl)-1-naphthalenesulphonamide (0.36 g), was suspended in N-methylpyrrolidone (1 ml) and freshly prepared 1M sodium methoxide in methanol (3 ml) was added. The reaction mixture was heated to reflux for 4 hours, cooled and evaporated to dryness. The residue was purified by flash chromatography on silica gel (5 g) eluting with a methanol/dichloromethane gradient to give 5-dimethylamino-N-(6-methoxy-3-pyridazinyl)-1-naphthalenesulphonamide (0.14 g), m.p. 125–127° C.; mass spectrum (+ve CI): 359 (M+N)$^+$.

EXAMPLE 40

Using an analogous procedure to that described in Example 39, but using sodium ethoxide in ethanol in place of sodium methoxide in methanol, there was obtained (in 27% yield) 5-dimethylamino-N-( 6-ethoxy-3-pyridazinyl)-1-naphthalenesulphonamide, m.p. 194–198ec; $^1$H NMR (d$_6$-DMSO, 200 MHz): 1.28 (t,3H), 2.62 (s,6H), 4.18 (q,2H), 7.23 (d,1H), 7.3 (d,1H), 7.7.38–7.68 (m,2H), 7.7–7.9 (m,1H), 8.25 (d,1H), 8.42 (t,2H), 13.75 (s,1H); mass spectrum (+ve FAB,DMSO/GLY): 373 (M+H)$^+$.

EXAMPLE 41

5-Dimethylamino-N-(6-chloro-3-pyridazinyl)-1-naphthalenesulphonamide (0.72 g) was dissolved in N,N-dimethylformamide and sodium thiomethoxide (0.42 g) added. The mixture was heated to 100° C. for 6 hours, then cooled and 7% aqueous citric acid solution (15 ml) was added with stirring. The solid formed was collected by filtration and washed with water (10 ml). The solid was then purified by chromatography on silica gel (20 g) under reduced pressure, eluting with an ethyl acetate/toluene gradient, to give 5-dimethylamino-N-(6-methylthio-3-pyridazinyl)-1-naphthalenesulphonamide (0.28 g), m.p. 188–190° C.; mass spectrum (+ve CI): 375 (M+H)$^+$.

EXAMPLES 42–45

Using an analogous procedure to that described in Example 1, but starting from the appropriate amino heterocycle of formula II, the following compounds of formula I were obtained (in yields of 25–53%):

EXAMPLE 42

5-Dimethylamino-N-(6-methyl-3-pyridazinyl)-1-naphthalenesulphonamide, m.p. 113–115° C.; mass spectrum (+ve FAB, DMSO/methanol/NBA): 342 (M)+; starting from 3-amino-6-methylpyridazine, which was obtained by an analogous procedure to that described in *J.Pharm.Soc (Japan)*, 1962, 82, 233;

EXAMPLE 43

5-Dimethylamino-N-(6-chloro-4,5-dimethyl-3-pyridazinyl)-1-naphthalenesulphonamide, m.p. 229–231° C.; mass spectrum (+ve FAB, DMSO/dichloromethane/NBA): 391 (M+H)+; starting from 3-amino-6-chloro-4,5-dimethylpyridazine, which was obtained by the procedure described in *J.Pharm.Soc.(Japan)*, 1962, 82, 233;

EXAMPLE 44

5-Dimethylamino-N-(2-bromo-5-pyrimidinyl)-1-naphthalenesulphonamide, m.p. 177–179° C.; mass spectrum (+ve FAB, DMSO/NBA): 407 (M+H)+; starting from 5-amino-2-bromopyrimidine, which was obtained by the procedure described in *Coll.Czech Chem. Comm.*, 1974, 40, 1348 and 1396; and

EXAMPLE 45

5-Dimethylamino-N-(5,6-dimethyl-2-pyrazinyl)-1-naphthalenesulphonamide, m.p. 191–192° C.; mass spectrum (+ve CI): 357 (M+H)+; starting from 2-amino-5,6-dimethylpyrazine, which was obtained by the procedure described in *J. Am. Chem. Soc.*, 1945, 67, 803.

EXAMPLE 46

Sodium hydride (60% dispersion in oil; 0.094 g) was added to a solution of 2-amino-5-bromo-3-methoxypyrazine (0.159 g) in dimethoxyethane (4 ml). The solution was stirred for 10 minutes and then 4-nitrophenyl 4'-isobutyl-2-biphenylsulphonate (0.321 g) was added. The solution was allowed to stand for 5 hours and then water (20 ml) was added. 2M Hydrochloric acid (2 ml) was added and the mixture was extracted with ethyl acetate (2×30 ml). The extracts were dried ($MgSO_4$) and volatile material was removed by evaporation. The residue was purified by elution with ethyl acetate/hexane (1:3 v/v) through a silica gel Mega Bond Elut column. The resulting solid was recrystallised from a mixture of ether and hexane to give N-(5-bromo-3-methoxy-2-pyrazinyl)-4'-isobutyl-2-biphenylsulphonamide (0.09 g), m.p. 154–156° C.; $^1$H NMR ($d_6$-DMSO): 0.9 (d,6H), 1.8–2.0 (m,1H), 2.5 (d,2H), 3.85 (s,3H), 7.1 (s,4H), 7.3 (d,1H), 7.5–7.7 (m,2H), 7.8 (br s,1H), 8.05 (d,1H), 10.2–10.3 (br, 1H); mass spectrum (+ve FAB, methanol/NBA): 478 (M+H)+.

The starting material 4-nitrophenyl 4'-isobutyl-2-biphenylsulphonate was obtained as follows:

(i) A solution of 2-iodobenzenesulphonyl chloride (obtained as described in *J. Org. Chem.* 1977, 42, 3265) (8.28 g) and 4-nitrophenol (3.81 g) in pyridine (50 ml) was heated at 100° C. for 3 hours. Volatile material was removed by evaporation and water (200 ml) was added to the residue. The mixture was extracted with ethyl acetate (2×200 ml) and the combined extracts were washed with 1M hydrochloric acid (2×200 ml) and dried ($MgSO_4$). Solvent was removed by evaporation and the residue was recrystallised from a mixture of ethyl acetate and hexane to give 4-nitrophenyl 2-iodobenzenesulphonate (7.83 g), m.p. 131–133° C.; mass spectrum (+ve CI): 405 (M+).

(ii) A mixture of 4-nitrophenyl 2-iodobenzenesulphonate (0.405 g), 4-isobutylphenylboronic acid (obtained as described in European Patent Application, publication No. 0569193) (0.179 g), tetrakis(triphenylphosphine)palladium (O) (0.058 g), toluene (15 ml), ethanol (10 ml) and 2M sodium carbonate solution (5.5 ml) was stirred vigorously and heated under reflux for 5 hours. Water (20 ml) was added and the mixture was extracted with ethyl acetate (2×25 ml). The combined extracts were washed with saturated sodium chloride solution (25 ml) and dried ($MgSO_4$). Volatile material was removed by evaporation and the residue was purified by elution with ethyl acetate/hexane (1:3 v/v) through a silica gel Mega Bond Elut column to give 4-nitrophenyl 4'-isobutyl-2-biphenylsulphonate (0.349 g); $^1$H NMR ($d_6$-DMSO): 0.9 (d,6H), 1.8–2.0 (m,1H), 2.5 (d,2H), 7.1–7.25 (m,4H), 7.35 (d,2H), 7.55 (d,1H), 7.7 (t,1H), 7.9 (t,1H), 8.05 (d,1H), 8.2 (d,2H); mass spectrum (+ve FAB, DMSO/methanol/NBA): 412 (M+H)+.

EXAMPLE 47

Using an analogous procedure to that described in Example 11, but using proportionate amounts of 2-amino-5-bromo-3-methoxypyrazine and naphthalene-1-sulphonyl chloride, there was thus obtained N-(5-bromo-3-methoxy-2-pyrazinyl)-1-naphthalenesulphonamide, m.p. 169–171° C.; mass spectrum (+ve CI); 394 (M+H)+.

EXAMPLE 48

Using an analogous procedure to that described in Example 11, but using proportionate amounts of 2-amino-5-bromo-3-methoxypyrazine and naphthalene-2-sulphonyl chloride, there was thus obtained N-(5-bromo-3-methoxy-2-pyrazinyl)-2-naphthalenesulphonamide, m.p. 182–184° C.; mass spectrum (+ve CI); 394(M+H)+.

EXAMPLE 49

Sodium hydride (oil free; 0.053 g) was added to a solution of 2-amino-5-bromo-3-methoxypyrazine (0.151 g) in DME (5 ml). The solution was stirred for 10 minutes and then a solution of 4'-methyl-2-biphenylsulphonyl chloride (0.198 g) in DME (2 ml) was added. The solution was allowed to stand for 1 hour and then water (25 ml) was added. 2M Hydrochloric acid (2 ml) was added and the mixture was extracted eith ethyl acetate (2×25 ml). The extracts were washed with water (25 ml) and saturated sodium chloride solution (25 ml) and dried ($MgSO_4$). Volatile material was removed by evaporation and the residue was recrystallised from ethyl acetate to give N-(5-bromo-3-methoxy-2-pyrazinyl)-4'-methyl-2-biphenylsulphonamide (0.12 g) m.p. 204–206° C.; $^1$H NMR ($d_6$-DMSO): 2.4 (s,3H), 3.85(s,3H), 7.05–7.2(m,4H), 7.3(dd,1H), 7.55–7.7(m,2H), 7.8(s,1H), 8.1(dd,1H); mass spectrum (+ve FAB, methanol/NBA): 436 (M+H)+.

The starting material 4'-methyl-2-biphenylsulphonyl chloride was obtained as follows:

(i) A mixture of 4-methylbenzeneboronic acid (0.272 g), 2-iodobenzenesulphonic acid, sodium salt, (0.612 g) (obtained as described in *J. Org. Chem*, 1977, 42, 3265), sodium carbonate (0.424 g) and 10% palladium on carbon (0.1 g) in ethanol (24 ml) and water (6 ml) was heated under reflux for 18 hours. The hot mixture was filtered through diatomaceous earth and the filtrate was concentrated and dried under vacuum. The residue was dissolved in a mixture of sulpholane (2 ml) and acetonitrile (2 ml). Phosphoryl chloride (0.73 ml) was added and the solution was heated at 70° C. for 1 hour. The solution was cooled to oIC and ice-vater (20 ml) was added dropwise. The mixture was extracted with ethyl acetate (2×25 ml) and the extracts were washed with water (4×25 ml) and saturated sodium chloride solution (25 ml) and dried ($MgSO_4$). Volatile material was removed by evaporation and the residue was purified by flash chromatography, eluting first with hexane and then with ethyl acetate/hexane (1:9 v/v), to give 4'-methyl-2-biphenylsulphonyl chloride (0.22 g); $^1$H NMR ($d_6$-DMSO); 2.35 (s,3H); 7.15–7.25 (m,3H), 7.25–7.45 (m,4H), 7.9–8.0 (m,1H); mass spectrum (+ve CI): 266(M+).

EXAMPLE 50

Sodium hydride (60% dispersion in oil; 0.198 g) was suspended in dimethoxyethane (5 ml) and 2-amino-5-bromo-3-methoxypyrazine (0.405 g) was added with stirring. After 15 minutes, 2-biphenylsulphonyl chloride (0.5 g) was added and the mixture was stirred for 18 hours. The reaction mixture was poured into water (20 ml) and acidified to pH2 with concentrated hydrochloric acid and extracted with ethyl acetate (3×25 ml). The combined organic extracts were evaporated and the residue was purified by flash chromatography on silica gel (30 g), eluting with hexane/ethyl acetate/glacial acetic acid (160/40/1 v/v), to give N-(5-bromo-3-methoxy-2-pyrazinyl)-2-biphenylsulphonamide (0.46 g); $^1$H NMR ($d_6$-DMSO): 3.82 (s,3H), 7.2–7.4(m,6H), 7.53–7.7(m,2H), 7.78(s,1H), 8.08 (dd,1H), 10.33(br,1H); mass spectrum (+ve FAB, methanol/NBA): 420(M+H)$^+$.

EXAMPLES 51–53

Using an analogous procedure to that described in Example 50, but starting from a proportionate amount of the appropriate amino heterocycle of formula II, the following compounds of formula Ib were obtained (in yields of 32–65%):

EXAMPLE 51

N-(5-chloro-3-methoxy-2-pyrazinyl)-2-biphenylsulphonamide, m.p. 155–158° C.; $^1$H NMR ($d_6$-DMSO, 200 MHz): 3.85 (s,3H), 7.2–7.4 (m, 6H), 7.53–7.75 (m,3H), 8.08 (dd,1H), 10.35 (br,1H) ; mass spectrum (+ve CI): 376(M+H)$^+$; starting from 2-amino-5-chloro-3-methoxypyrazine;

EXAMPLE 52

N-(3-methoxy-5-methyl-2-pyrazinyl)-2-biphenylsulphonamide, m.p. 122–126° C.; $^1$H NMR ($d_6$-DMSO, 200 MHz): 2.26 (s,3H), 3.81 (s,3H), 7.17–7.43 (m,5H), 7.47–7.69 (m,1H), 8.07 (dd,1H), 9.64 (br,1H); mass spectrum (+ve FAB, methanol/GLY): 356(M+H)$^+$; starting from 2-amino-3-methoxy-5-methylpyrazine; and

EXAMPLE 53

N-(2-chloro-4-methoxy-5-pyrimidinyl)-2-biphenylsulphonamide, m.p. 152–154° C.; mass spectrum (+ve CI): 376(M+H)$^+$; starting from 5-amino-2-chloro-4-methoxypyrimidine.

EXAMPLE 54

Using an analogous procedure to that described in Example 38, there was thus obtained 5-dimethylamino-N-(5-ethynyl-3-methoxy-2-pyrazinyl)-1-naphthalenesulphonamide (in an overall yield of 19%); $^1$H NMR ($d_6$-DMSO): 2.83(s,6H), 3.90(s,3H), 4.43(s,1H), 7.25 (d,1H), 7.54–7.78(m,3H), 8.3–8.53(m,3H), 11.5(br,1H); mass spectrum (+ve FAB, methanol/NBA); 383(M+H)$^+$; starting from a proportionate amount of 5-dimethylamino-N-[3-methoxy-5-(2-trimethylsilyl-1-ethynyl)-2-pyrazinyl]-1-naphthalenesulphonamide, itself obtained using an analogous procedure to that described in Example 38, part (i), starting from 5-(dimethylamino)-N-(5-bromo-3-methoxy-2-pyrazinyl)-1-naphthylenesulphonamide.

EXAMPLE 55

5-Acetamido-N-(5-bromo-3-methoxy-2-pyrazinyl)-1-naphthalene sulphonamide (1.0 g) was suspended in ethanol (22 ml) and a solution of 48% hydrobromic acid in water (3 ml) was added. The resulting mixture was stirred and heated at reflux for 4 hours. The solution was cooled and basified to pH 4 by the addition of aqueous ammonia (d=0.88). The yellow solid which formed was extracted into ethyl acetate (3×50 ml) and the combined extracts were washed with brine (100 ml) and dried ($MgSO_4$). Volatile material was removed by evaporation and the residue (0.7 g) was dissolved in a mixture of acetic acid (1.4 ml), ethanol (3 ml), acetone (0.9 ml) and sodium acetate (0.28 g). Sodium cyanoborohydride (0.58 g)was added portionwise to this stirred mixture under a nitrogen atmosphere over a period of 5 minutes, while maintaining the temperature at 0° C. Stirring was continued for a further 5 minutes. The mixture was basified to pH 8 by the addition of saturated aqueous sodium bicarbonate solution and volatile materials were removed by evaporation. The residue was extracted with ethyl acetate (3×75 ml) and the combined extracts were dried ($MgSO_4$). Volatile material was removed by evaporation and the residue was purified by elution with dichloromethane through a silica gel Mega Bond Elut column. There was thus obtained N-(5-bromo-3-methoxy-2-pyrazinyl)- 5-(isopropylamino)-1-napbthalenesulphonamide (0.07 g); $^1$H NMR (d $_6$-DMSO): 1.25(d,6H), 3.34–3.49 (m,1H), 3.90 (s,3H), 6.63 (d,1H), 7.38–7.56 (m,2H), 7.74 (s,1H), 7.92 (d,1H), 8.25 (d,1H), 8.53 (d,1H), 11.4 (br,1H); mass spectrum (+ve FAB, DMSO/NBA); 451(M+H)$^+$.

EXAMPLE 56

5-(N-Benzyloxycarbonyl-N-methylamino)-N-(5-bromo-3-methoxy-2-pyrazinyl)-1-naphthalenesulphonamide (0.40 g) was suspended in 33% hydrobromic acid in acetic acid (5 ml) and the mixture was stirred for 1 hour. Evaporation afforded a yellow residue which was dissolved in water (20 ml ), basified to pH 10 with 1N aqueous sodium hydroxide and extracted with ethyl acetate (3×25 ml). The combined organic extracts were dried ($MgSO_4$) and evaporated. The residue was purified by flash chromatography on silica gel (30 g), eluting with a gradient of 20–50% ethyl acetate in hexane, affording 5-(N-benzyl-N-methyl-amino)-N-(5-bromo-3-methoxy2-pyrazinyl)-1-naphthalenesulphonamide (0.095 g); $^1$H NMR ($d_6$DMSO): 2.72 (s,3H), 3.90 (s,3H), 4.25 (s,2H), 7.2–7.4 (m,6H), 7.58 (t,1H), 7.68 (t,1H), 7.80 (s,1H), 8.32 (dd,1H), 8.46 (d,1H), 8.64 (d,1H), 11.48 (br, 1H); mass spectrum (+ve FAB, methanol/NBA); 513(M+H)$^+$.

The starting material 5-(N-benzyloxycarbonyl-N-methylamino)-N-(5-bromo-3-methoxy-2-pyrazinyl)-1-naphthalenesulphonamide was obtained as follows:

(i) Sodium hydride (60% dispersion in oil; 0.795 g) was added to a stirred mixture of sodium 5-(N- benzyloxycarbonylamino)-1-naphthalenesulphonate (3.0 g) (obtained as described in Synlett., 1992, 661) in N,N-dimethylformamide (30 ml). After a period of 10 minutes, methyl iodide (0.48 ml) was added and the reaction was allowed to stir for 2 hours. A further aliquot of methyl iodide (0.26 ml) was added and stirring was continued for 18 hours. The resulting mixture was poured into water (25 ml), acidified to pH3 with concentrated hydrochloric acid and extracted with ethyl acetate (3×50 ml). Combined organic extracts were evaporated to give a viscous oil (2.1 g) which was dissolved in N,N-dimethylformamide (12 ml) and thionyl chloride (0.78 ml) was added at 0° C. The mixture was stirred for 30 minutes at 0° C. then poured onto ice (100 g) and extracted with ethyl acetate (3×50 ml). The combined organic extracts were evaporated to give 5-(N-benzyloxycarbonyl-N-methylamino)-1-naphthalenesulphonyl chloride (1.42 g); $^1$H NMR (d$_6$-DMSO): 3.29 (s,3H), 4.98 (br,2H), 7.04 (br,1H), 7.22 (br, 2H), 7.43–7.6 (m,5H), 7.70 (d,1H), 7.99 (dd,1H), 8.85 (d,1H); mass spectrum (−ve FAB, DMSO/methanol/GLY): 370 (M−H)$^−$.

(ii) 2-Amino-5-bromo-3-methoxypyrazine (0.3 g) was added to a stirred suspension of sodium hydride (60% dispersion in oil; 0.15 g) in dimethoxyethane (5 ml). After 10 minutes, 5-(N-benzyloxycarbonyl-N-methylamino)-1-naphthalenesulphonyl chloride (0.6 g) in dimethoxyethane (2 ml) was added and stirring was continued for 2 hours. The mixture was poured into water (20 ml) and washed with ethyl acetate (20 ml). The aqueous layer was acidified with concentrated hydrochloric acid to pH2 and extracted with ethyl acetate (3×50 ml). The combined organic extracts were dried (MgSO$_4$) and evaporated. The residue was purified by flash chromatography on silica gel (25 g), eluting with a gradient of 20–50% ethyl acetate in hexane to give 5-(N-benzyloxycarbonyl-N-methylamino)-N-(5-bromo-3-methoxy-2-pyrazinyl)-1-naphthalenesulphonamide (0.50 g) as a white foam; $^1$H NMR (d$_6$-DMSO): 3.34 (s,3H), 3.90 (s,3H), 5.08 (br,2H), 6.95 (br,1H), 7.19 (br,2H), 7.22–7.56 (m,2H), 7.6–7.77 (m,3H), 7.79 (s,1H), 8.07 (d,1H), 8.37 (dd,1H), 8.80 (d,1H), 11.58 (br,1H); mass spectrum (+ve FAB, DMSO/NBA): 557(M+H)$^+$.

EXAMPLE 57

5-(N-Benzyloxycarbonylamino)-N-(5-bromo-3-methoxy-2-pyrazinyl)-1-naphthalenesulphonamide (0.7 g) was dissolved in 33% hydrobromic acid in acetic acid (14 ml) and the resulting solution was stirred for 1 hour. Diethyl ether (60 ml) was added and after 10 minutes further stirring, the mixture was filtered. The solid was dissolved in water (5 ml), basified to pH 8 by the addition of 1N aqueous sodium hydroxide and extracted with ethyl acetate (3×25 ml). The combined organic extracts were evaporated and the residue was purified by flash chromatography on silica gel (10 g), eluting with a gradient of 20–50% ethyl acetate in hexane to give 5-amino-N-(5-bromo-3-methoxy-2-pyrazinyl)-1-naphthalenesulphonamide (0.07 g); $^1$H NMR (d$_6$-DSO): 3.82 (s,3H), 6.78 (d,,H), 7.35 (t,(H), 7.50 (t,(H), 7.78 (s,1H), 7.91 (d,2H), 8.25 (d,2H), 8.40 (d,1H); mass spectrum (+ve FAB, methanol/NBA): 409 (M+H)$^+$.

The starting material 5-(N-benzyloxycarbonylamino)-N-(5-bromo-3-methoxy-2-pyrazinyl)-1-naphthalenesulphonamide was prepared using an analogous procedure to that described in Example 36, starting from proportionate amounts of 2-amino-5-bromo-3-methoxypyrazine and 5-(N-benzyloxycarbonylamino)-1-naphthalenesulphonyl chloride (obtained as described in Synlett., 1992, 661), in a yield of (11%; m.p. 226–228° C.; mass spectrum (+ve FAB, methanol/NBA): 543 (M+H)$^+$.

EXAMPLES 58–60

Using an analogous procedure to that described in Example 46, but starting from the appropriate amino heterocycle of formula II, the following compounds of formula I were obtained:

EXAMPLE 58

4'-Isobutyl-N-(3-methoxy-5-methyl-2-pyrazinyl)-2-biphenylsuophonamide, m.p. 127–128° C.; $^1$H NMR (d$_6$DMSO): 0.9 (d,6H), 1.8–2.0 (m,1H), 2.3 (s,3H), 2.5 (d,2H), 3.8 (s,3H), 7.1 (s,4H), 7.25 (d, 1H), 7.5–7.65 (m,3H), 8.1 (d,1H), 9.4 (s,1H); mass spectrum (+ve CI): 412 (M+H)$^+$; starting from 2-amino-3-methoxy-5-methylpyrazine;

EXAMPLE 59

N-(5-Chloro-3-methoxy-2-pyrazinyl)-4'-isobutyl-2-biphenylsulphonamide, m.p. 166–168° C.; $^1$H NMR (d$_6$-DMSO): 0.9 (d,6H), 1.8–2.0 (m,1H), 2.5 (d, 2H), 3.8 (s,3H), 7.1–7.2 (m,1H), 7.3 (d,2H), 7.5–7.7 (m,3H), 8.0 (d,1H), 10.35 (s,1H); mass spectrum (+ve CI): 432(M+H)$^+$; starting from 2-amino-5-chloro-3-methoxypyrazine; and

EXAMPLE 60

N-(6-Chloro-3-pyridazinyl)-4'-isobutyl-2-biphenylsulphonamide, m.p. 166–168° C.; NMR (d$_6$-DMSO+CD$_3$CO$_2$D): 0.9 (d,6H), 1.75–1.9 (m, 2H), 2.4 (d,2H), 7.0 (d,2H), 7.2 (d,2H), 7.3 (d,1H), 7.45 (s,2H), 7.5–7.65 (m,2H), 8.15 (d,1H); mass spectrum (+ve FAB, DMSO/methanol/GLY): 402(M+H)$^+$; starting from 3-amino-6-chloropyridazine.

EXAMPLE 61

Using an analogous procedure to that described in Example 49, but starting from 4'-methoxy-2-biphenylsulphonyl chloride, there was thus obtained N-(5-bromo-3-methoxy-2-pyrazinyl)-4'-methoxy-2-biphenylsulphonamide, m.p. 160–162° C.; $^1$H NMR (d$_6$-DMSO): 3.8 (s,3H), 3.9 (s,3H), 6.9 (d,2H), 7.15 (d,2H), 7.3 (d,1H), 7.5–7.7 (m,2H), 7.75 (s,1H), 8.1 (d,1H), 10.15 (br,1H); mass spectrum (+ve FAB, DMSO/methanol/NBA): 450 (M+H)$^+$.

The starting material 4'-methoxy-2-biphenylsulphonyl chloride was prepared in 61% yield by an analogous procedure to that described in Example 49, part (i); $^1$H NMR (CDCl$_3$): 3.9 (s,6H), 6.95 (d,2H), 7.35 (d,2H), 7.4 (d,1H), 7.6 (t,1H), 7.7 (t,1H), 8.2 (d,1H); mass spectrum (+ve EI): 282(M$^+$); starting from 4-methoxybenzeneboronic acid.

EXAMPLE 62

Using an analogous procedure to that described in Example 61, but starting from 2-amino-3-methoxy-5-methylpyrazine, there was thus obtained 4'-methoxy-N-(3-methoxy-5-methyl-2-pyrazinyl)-2-biphenylsulphonamide, m.p. 146–149° C.; $^1$H NMR (d$_6$-DMSO): 2.3 (s,3H), 3.8 (s,6H), 6.9 (d,2H), 7.15 (d,2H), 7.25 (d,1H), 7.4–7.65 (m,3H), 8.1 (d,1H), 9.6 (br s,1H); mass spectrum (+ve FAB, DMSO/NBA): 386(M+H)$^+$.

EXAMPLE 63

2 M Sodium hydroxide solution (0.6 ml) was added to a solution of N-(isobutoxycarbonyl)-N-(3-methoxy-5-methyl- 2-pyrazinyl)-4'-methyl-2-biphenylsulphonamide (0.232 g) in methanol (2.4 ml) and dimethoxyethane (2.4 ml) and the mixture was stirred for 2 hours. Volatile material was removed by evaporation and water (10 ml) was added to the residue. The mixture was acidified with 2M hydrochloric acid and extracted with ethyl acetate (2×10 ml). The extracts were washed with water (10 ml) and saturated sodium chloride solution (10 ml) and dried ($MgSO_4$). The solvent was removed by evaporation and the residue was recrystallised from ethanol to give N-(3-methoxy-5-methyl-2-pyrazinyl)-4'-methyl-2-biphenylsulphonamide (0.1 g) m.p. 184–185° C.; $^1$H NMR ($d_6$-DMSO): 2.3 (s,3H), 2.4 (s,3H), 3.6 (s,3H), 7.05–7.3 (m,5H), 7.45–7.7 (m,3H), 8.1 (dd,1H), 9.35–9.45 (br s,1H); mass spectrum (−ve FAB, DMSO/Methanol/GLY): 368 (M−H)⁻.

The starting material N-(isobutoxycarbonyl)-N-(3-methoxy-5-methyl-2-pyrazinyl)-4"-methyl-2-biphenylsulphonamide was obained as follows:

(i) 2-Iodobenzenesulphonyl chloride (obtained as described in *J Org Chem*, 1977, 42, 3265) (12.1 g) was added to a solution of 2-amino-3-methoxy-5-methylpyrazine (5.6 g) in pyridine (100 ml) and the solution was heated at 70° C. for 8 hours. Volatile material was removed by evaporation and water (200 ml) was added to the residue. The mixture was extracted with ethyl acetate (2×200 ml) and the extracts were washed with 2M hydrochloric acid (200 ml) and water (200 ml). The extracts were dried ($MgSO_4$) and the solvent was removed by evaporation. The residue was triturated with ether to give N-(3-methoxy-5-methyl-2-pyrazinyl)-2-iodobenzenesulphonamide (7.2 g), m.p. 136–138° C.; $^1$H NMR ($d_6$-DMSO): 2.3 (s,3H), 3.9 (s,3H), 7.3 (dt,1H), 7.5–7.65 (m,2H), 8.05–8.15 (m,2H), 10.7–10.8 (br s, 1H).

(ii) Isobutyl chloroformate (0.58 ml) was added dropwise to a stirred solution of N-(3-methoxy-5-methyl-2-pyrazinyl)-2-iodobenzenesulphonamide (1.65 g), triethylamine (0.57 ml) and pyridine (0.16 ml) in dichloromethane (30 ml) under an atmosphere of argon. The mixture was stirred for 2 hours and then 2H hydrochloric acid (20 ml) was added. The organic layer was separated, washed with water (20 ml) and saturated sodium chloride solution (20 ml) and dried ($MgSO_4$). Volatile material was removed by evaporation and the residue was purified by flash chromatography, eluting with ethyl acetate/hexane (1:4 v/v), to give N-(isobutoxycarbonyl)-N-(3-methoxy-5-methyl-2-pyrazinyl)-2-iodobenzenesulphonamide (2.0 g) as a gum; $^1$H NMR ($d_6$-DMSO): 0.7 (d,2H), 1.6–1.8 (m,1H), 2.5 (s,3H), 3.9 (d,2H), 4.0 (s,3H), T.4 (dt,1H), 7.7 (dt,1H), 8.15 (s,1H), 8.2 (dd,1H), 8.35 (dd,1H).

(iii) A mixture of N-(isobutoxycarbonyl)-N-(3-methoxy-5-methyl-2-pyrazinyl)-2-iodobenzenesulphonamide (0.252 g) 4-methylbenzeneboronic acid (0.068 g), tetrakis(triphenylphosphine)palladium(0) (0.0115 g), toluene (2.5 ml), ethanol (1.25 ml) and 2H sodium carbonate solution (3.75 ml) was stirred vigorously and heated under reflux for 2 hours under an atmosphere of argon. Water (10 ml) was added and the mixture was extracted with ethyl acetate (2×10 ml). The combined extracts were washed with saturated sodium chloride solution (25 ml) and dried ($MgSO_4$). Volatile material was removed by evaporation and the residue was purified by flash chromatography, eluting with ethyl acetate/hexane (1:4 v/v), to give N-(isobutoxycarbonyl)-N-(3-methoxy-5-methyl-2-pyrazinyl)-4'-methyl-2-biphenylsulphonamide (0.182 g); $^1$H NMR (DMSO-$d_6$): 0.6 (d,6H), 1.55–1.75 (m,1H), 2.35 (s,3H), 2.5 (s,3H), 3.85 (d,2H), 3.95 (s,3H), 7.15–7.25 (m,4H), 7.35–7.45 (m,1H), 7.7–7.8 (m,2H), 8.15 (s,1H), 8.45–8.55 (m,1H); mass spectrum (+ve FAB, methanol/NBA): 470 (M+H)⁺.

EXAMPLES 64–65

Using an analogous procedure to that described in Example 63, the following compounds of formula I were obtained in yields of 68–86%:

EXAMPLE 64

4'-Chloro-N-(3-methoxy-5-methyl-2-pyrazinyl)-2-biphenylsulphonazide, m.p. 127–128° C.; mass spectrum (+ve FAB, DMSO/methanol/NBA): 390 (M+H)⁺; starting from 4'-chloro-N-(isobutoxycarbonyl)-N-(3-methoxy-5-methyl-2-pyrazinyl)-2-biphenylsulphonamide; $^1$H NMR ($d_6$-DMSO); 0.5 (d,6H), 1.4–1.6 (m,1H), 2.4 (s,3H), 3.7 (d,2H), 3.8 (s,3H), 7.2–7.4 (m,4H), 7.6–7.7 (m, 2H), 8.0 (s,1H), 8.3–8.4 (m,1H), 8.35 (dd,1H); mass spectrum (+ve FAB, DMSO/methanol/NBA): 490 (M+H)⁺; itself obtained using an analogous procedure to that described in Example 63, part (iii) but using 4-chlorobenzeneboronic acid.

EXAMPLE 65

3'-Amino-N-(3-methoxy-5-methyl-2-pyrazinyl)-2-biphenylsulphonamide; $^1$H NMR ($d_6$-DMSO): 2.25 (s,3H), 3.85 (s,3H), 6.3–6.4 (m,2H), 6.5–6.65 (m, 1H), 6.9–7.1 (M,1H), 7.25 (dd,1H), 7.4–7.7 (m, 3H), 8.05 (dd,1H); mass spectrum (+ve CI); 432 (M+H)⁺; starting from 3'-amino-N-(isobutoxycarbonyl)-N-(3-methoxy-5-methyl-2-pyrazinyl)-2-biphenylsuiphonamide; $^1$N NMR ($d_6$DMSO): 0.6 (d,6H), 1.5–1.7 (m,fH), 2.5 (s,3H), 3.8 (d,2H), 3.9 (s,3H), 5.05–5.15 (br s,1H), 6.4–6.6 (m,3H), 7.0 (t,1H), 7.3–7.4 (m,1H), 7.65–7.75 (m, 2H), 8.15 (s,1H), 8.4–8.5 (m,1H); mass spectrum (+ve FAB, DMSO/NBA): 471 (M+H)⁺; itself obtained using an analogous precedure to that described in Example 63, part (iii) but using 3-aminobenzeneboronic acid.

EXAMPLE 66

4'-Isobutyl-3'-nitro-2-biphenylsulphonyl chloride (0.353 g) was added to a solution of 2-amino-3-methoxy-5-methylpyrazine (0.139 g) in pyridine (10 ml) at 0° C. The solution w?as heated at 75° C. for 18 hours and then volatile material was removed by evaporation. The residue was purified by elution with dichloromethane through a silica gel Mega Bond Elut column and the resulting foam was triturated with ether/hexane (1:1 v/v) to give 4'-isobutyl-N-(3-methoxy-5-methyl-2-pyrazinyl)-3'-nitro-2-biphenylsulphonamide (0.18 g), m.p. 114–115° C.; mass spectrum (+ve CI): 457 (M+H)⁺.

The starting 4'-isobutyl-3'-nitro-2-biphenylsulphonyl chloride was obtained as follows:

(i) Using an analogous precedure to that described in Example 49, part (i), but starting from 4-isobutylbenzeneboronic acid, there was obtained (in 46% yield) 4'-isobutyl-2-biphenylsulphonyl chloride; 1H NNR ($CDCl_3$): 0.95 (d,6H); 1.8–2.0 (m,1H), 2.55 (d,2H), 7.25 (d,2H), 7.4 (d,2H), 7.45.(d,2H), 7.6 (t,1H), 7.7 (t,1H), 8.7 (d,1H); mass spectrum (+ve CI): 308(M⁺).

(ii) Fuming nitric acid (0.8 ml) was added over 10 minutes to a stirred solution of 4'-isobutyl-2-biphenylsulphonyl chloride (3.09 g) in acetic anhydride (18 ml) at −20° C. The solution was kept at −20° C. for 1.5 hours and then allowed to warm to ambient temperature. The solution was stirred for 1.5 hours and then added to ice (300 g) with vigorous sextracted with ether 30 minutes and extracted with ether (3×100 ml) while still below 10° C. The ethereal solution was dried (MgSO$_4$) and the solvent was removed by evaporation. The resulting oil was purified by flash chromatography, eluting with ethyl acetate/hexane (1:9 v/v), to give 4'-isobutyl-3'-nitro-2-biphenylsulphonyl chloride (2.01 g); $^1$H NMR (CDCl$_3$): 0.95 (d,6H), 1.9–2.05 (m,1H), 2.9 (d,2H), 7.35–7.5 (m,2H), 7.6 (d,1H), 7.7 (d,1H), 7.8 (t,1H), 8.0 (s,1H), 8.25 (d,1H); mass spectrum (EI): 353 (M$^+$).

EXAMPLE 67

4-Isobutyl-$\underline{N}$-(3-methoxy-5-methyl-2-pyrazinyl)-3'-nitro-2-biphenylsulphonamide (0.456 g) was dissolved in methanol/water (1:9 v/v; 10 ml) and the solution was catalytically hydrogenated over 10% Pd-C (0.046 g). The catalyst was removed by filtration through diatomaceous earth and the residue was purified by elution with ethyl acetate/hexane (1:3 v/v) through a silica gel Mega Bond Elut column. The resulting foam was recrystallised from ether to give 3'-amino-4'-isobutyl-$\underline{N}$-(3-methoxy-5-methyl-2-pyrazinyl)-2-biphenylsulphonamide (0.14 g), m.p. 160–162° C.; mass spectrum (+ve FAB, DMSO/methanol/NBA): 427 (M+H)$^+$.

EXAMPLE 68

Note: All Parts By Weight

The compounds of the invention may be administered for therapeutic or prophylactic use to warm-blooded animals such as man in the form of conventional pharmaceutical compositions, typical examples of which include the following:

| a) Capsule (for oral administration) | |
|---|---|
| Active ingredient * | 20 |
| Lactose powder | 578.5 |
| Magnesium stearate | 1.5 |

| b) Tablet (for oral administration) | |
|---|---|
| Active ingredient * | 50 |
| Microcrystalline cellulose | 400 |
| Starch (pregelatinised) | 47.5 |
| Magnesium stearate | 2.5 |

| c) Injectable Solution (for intravenous administration) | |
|---|---|
| Active ingredient * | 0.05–1.0 |
| Propylene glycol | 5.0 |
| Polyethylene glycol (300) | 3.0–5.0 |
| Purified water | to 100% |

| d) Injectable Suspension (for intramuscular administration) | |
|---|---|
| Active ingredient * | 0.05–1.0 |
| Methylcellulose | 0.5 |
| Tween 80 | 0.05 |
| Benzyl alcohol | 0.9 |
| Benzalkonium chloride | 0.1 |
| Purified water | to 100% |

Note: the active ingredient * may typically be an Example described hereinbefore or as a pharmaceutically acceptable salt. Tablets and capsules formulations may be coated in conventional manner in order to modify or sustain dissolution of the active ingredient. Thus, for example, they may be coated with a conventional enterically digestible coating.

Chemical Formulae

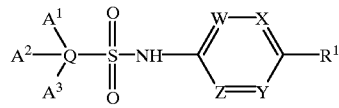

I

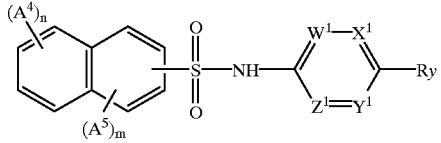

Ia

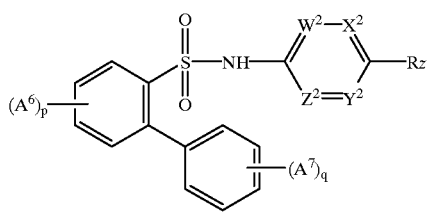

Ib

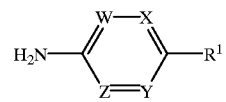

II

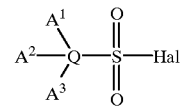

III

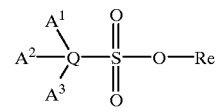

IIIa

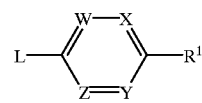

IV

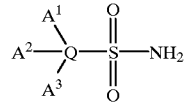

V

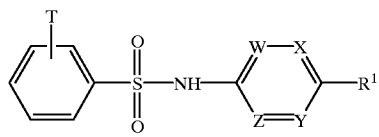

VI

What we claim is:

1. A compound having the formula VII;

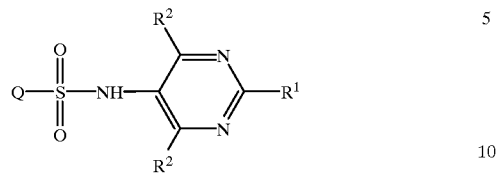

wherein:
Q is a naphthyl or biphenyl group which is either unsubstituted or is substituted at one, two, or three positions with $A^1$;

$A^1$ and $R^2$ are independently selected at each occurrence from hydrogen, $C_1$–$C_6$-alkoxy, di-halogeno-$C_1$–$C_6$-alkoxy, tri-halogeno-$C_1$–$C_6$-alkoxy, phenyl, phenoxy, phenyl-$C_1$–$C_6$-alkoxy, $C_1$–$C_6$-alkyl, amino-$C_1$–$C_6$-alkyl, hydroxy-$C_1$–$C_6$-alkyl, N-[$C_1$–$C_4$-alkyl]amino-$C_1$–$C_6$-alkyl, N,N-[di-$C_1$–$C_4$-alkyl]amino-$C_1$–$C_6$-alkyl, $C_2$–$C_6$-alkenyl, $C_2$–$C_6$-alkynyl, halogeno-$C_1$–$C_6$-alkyl, $C_2$–$C_6$-alkenyloxy, $C_1$–$C_4$-alkoxy-$C_1$–$C_6$-alkyl, $C_1$–$C_4$-alkylthio-$C_1$–$C_6$-alkyl, $C_1$–$C_4$-alkylsulphinyl-$C_1$–$C_6$-alkyl, $C_1$–$C_4$-alkylsulphonyl-$C_1$–$C_6$-alkyl, $C_3$–$C_6$-cycloalkyl, $C_3$–$C_8$-cycloalkyl-$C_1$–$C_6$-alkyl, phenyl-$C_1$–$C_6$-alkyl, halogeno, hydroxy, mercapto, cyano, nitro, carboxy, $C_1$–$C_6$-alkoxycarbonyl, $C_2$–$C_6$-alkenyloxycarbonyl, phenyloxycarbonyl, phenyl-$C_1$–$C_6$-alkoxycarbonyl, $C_1$–$C_6$-alkanoyl, benzoyl, $C_1$–$C_6$-alkylthio, $C_1$–$C_6$-alkylsulphinyl, $C_1$–$C_6$-alkylsulphonyl, phenylthio, phenylsulphinyl, phenylsulphonyl, $C_1$–$C_6$-alkanoylamino, trifluoroacetyl, trifluoroacetamido, N-[$C_1$–$C_4$-alkyl]trifluoroacetamido, benzamido, N-[$C_1$–$C_4$-alkyl]benzamido, carbamoyl, $C_1$–$C_4$-alkylcarbamoyl, di-$C_1$–$C_4$-alkylcarbamoyl, phenylcarbamoyl, sulphamoyl, N-$C_1$–$C_4$-alkylsulphamoyl, N,N-di-$C_1$–$C_4$-alkylsulphamoyl, N-phenylsulphamoyl, $C_1$–$C_6$-alkanesulphonamido, benezenesulphonamido, ureido, 3-$C_1$–$C_6$-alkylureido, 3-phenylureido, thioureido, 3-$C_1$–$C_6$-alkylthioureido and 3-phenylthioureido; or $A^1$ and $R^2$ independently are a group —NRaRb, in which Ra and Rb are independently selected from hydrogen, $C_1$–$C_6$-alkyl, phenyl-$C_1$–$C_4$-alkyl and $C_1$–$C_6$-alkyl bearing a carboxy or $C_1$–$C_4$-alkoxycarbonyl group; or $A^1$ and $R^2$ independently are a group —NRaRb in which Ra and Rb taken together complete a 1-pyrrolidinyl, 2-oxo-1-pyrrolidinyl, 1-piperidinyl or 2-oxo-1-piperidinyl ring;

$R^1$ is selected from 2-[$C_1$–$C_6$-alkoxycarbonyl]ethenyl, 2-phenylethenyl, $C_2$–$C_6$-alkynyl, $C_1$–$C_6$-alkoxycarbonylethynyl, phenylethynyl, $C_1$–$C_3$-alkoxy, dihalogeno-$C_1$–$C_3$-alkoxy, trihalogeno-$C_1$–$C_3$-alkoxy, phenyl-$C_1$–$C_3$-alkoxy, $C_1$–$C_6$-alkyl, amino-$C_1$–$C_6$-alkyl, hydroxy-$C_1$–$C_6$-alkyl, N-[$C_1$–$C_4$-alkyl]amino-$C_1$–$C_6$-alkyl, N,N-[di-$C_1$–$C_6$-alkyl]amino-$C_1$–$C_6$-alkyl, $C_2$–$C_6$-alkenyl, $C_2$–$C_6$-alkynyl, halogeno-$C_1$–$C_6$-alkyl, $C_2$–$C_6$-alkenyloxy, $C_1$–$C_4$-alkoxy-$C_1$–$C_6$-alkyl, $C_1$–$C_4$-alkylthio-$C_1$–$C_6$-alkyl, $C_1$–$C_4$-alkylsulphinyl-$C_1$–$C_6$-alkyl, $C_1$–$C_4$-alkylsulphonyl-$C_1$–$C_6$-alkyl, $C_3$–$C_6$-cycloalkyl, $C_3$–$C_8$-cycloalkyl-$C_1$–$C_6$-alkyl, phenyl-$C_1$–$C_6$-alkyl, halogeno, hydroxy, mercapto, cyano, nitro, carboxy, $C_1$–$C_6$-alkoxycarbonyl, $C_2$–$C_6$-alkenyloxycarbonyl, phenyloxycarbonyl, phenyl-$C_1$–$C_6$-alkoxycarbonyl, $C_1$–$C_6$-alkanoyl, benzoyl, $C_1$–$C_6$-alkylthio, $C_1$–$C_6$-alkylsulphinyl, $C_1$–$C_6$-alkylsulphonyl, phenylthio, phenylsulphinyl, phenylsulphonyl, $C_1$–$C_6$-alkanoylamino, trifluoroacetyl, trifluoroacetamido, N-[$C_1$–$C_4$-alkyl]trifluoroacetamido, benzaamido, N-[$C_1$–$C_4$-alkyl]benzamido, carbamoyl, $C_1$–$C_4$-alkylcarbamoyl, di-$C_1$–$C_4$-alkylcarbamoyl, phenylcarbamoyl, sulphamoyl, N-$C_1$–$C_4$-alkylsulphamoyl, N,N-di-$C_1$–$C_4$-alkylsulphamoyl, N-phenylsulphamoyl, $C_1$–$C_6$-alkanesulphonamido, benezenesulphonamido, ureido, 3-$C_1$–$C_6$-alkylureido, 3-phenylureido, thioureido, 3-$C_1$–$C_6$-alkylthioureido and 3-phenylthioureido; or $R^1$ is a group —NRaRb, in which Ra and Rb are independently selected from hydrogen, $C_1$–$C_6$-alkyl, phenyl-$C_1$–$C_4$-alkyl and $C_1$–$C_6$-alkyl bearing a carboxy or $C_1$–$C_4$-alkoxycarbonyl group; or $R^1$ is the group —NRaRb in which Ra and Rb taken together complete a 1-pyrrolidinyl, 2-oxo-1-pyrrolidinyl, 1-piperidinyl or 2-oxo-1-piperidinyl ring;

where any phenyl, naphthyl or benzene moiety of $A^1$, $R^1$ or $R^2$ is either unsubstituted or is substituted at one or two positions, with substituents independently selected at each occurrence from $C_1$–$C_4$-alkyl, $C_1$–$C_4$-alkoxy, halogeno, cyano and trifluoromethyl; or a pharmaceutically-acceptable salt of any foregoing compound.

2. A compound or pharmaceutically-acceptable salt according to claim 1, wherein:

Q is either unsubstituted or is substituted at one, two, or three positions, with $A^1$;

$A^1$ is independently selected at each occurrence from hydrogen, propoxy, isopropoxy, butoxy, 2-phenylpropoxy, 3-phenylpropoxy, cyano, methyl, ethyl, propyl, isopropyl, sec-butyl, aminomethyl, 2-aminoethyl, hydroxymethyl, 1-hydroxyethyl, 2-hydroxyethyl, methylaminomethyl, methylaminoethyl, dimethylaminomethyl, 2-(dimethylamino)ethyl, vinyl, allyl, 1-propenyl, 2-butenyl, ethynyl, 1-propynyl, 2-propynyl, 1-butynyl, chloromethyl, bromomethyl, fluoromethyl, dichloromethyl, difluoromethyl, trifluoromethyl, 2,2,2-trifluoroethyl, pentafluoroethyl, methoxy, ethoxy, difluoromethoxy, trifluoroethoxy, 2,2,2-trifluoroethoxy, 3,3,3-trifluoropropoxy, vinyloxy, allyloxy, 1-propenyloxy, 2-butenyloxy, methoxymethyl, ethoxymethyl, 1-methoxyethyl, 2-methoxyethyl, 2-ethoxyethyl, 3-methoxypropyl, methylthiomethyl, 1-methylthioethyl, 2-methylthioethyl, 2-methylthioprop-2-yl, ethylthiomethyl, 1-ethylthioethyl, 2-ethylthioethyl, 2-ethylthioprop-2-yl, methylsulphinylmethyl, 1-methylsulphinylethyl, 2-methylsulphinylethyl, 2-methylsulphinylprop-2-yl, ethylsulphinylmethyl, 1-ethylsulphinylethyl, 2-ethylsulphinylethyl, 2-ethylsulphinylprop-2-yl, methylsulphonylmethyl, 1-methylsulphonylethyl, 2-methylsulphonylethyl, 2-methylsulphonylprop-2-yl, ethylsulphonylmethyl, 1-ethylsulphonylethyl, 2-ethylsulphonylethyl, 2-ethylsulphonylprop-2-yl, cyclopropyl, cyclobutyl, cyclopentyl, cyclopropylmethyl, cyclopropylethyl, cyclobutylmethyl, cyclopentylmethyl, phenyl, benzyl, 1-phenylethyl, 2-phenylethyl, phenoxy, benzyloxy, 1-phenylethoxy, 2-phenylethoxy, fluoro, chloro, bromo, iodo, hydroxy, mercapto, nitro, carboxy, methoxycarbonyl, ethoxycarbonyl, propoxycarbonyl, allyloxycarbonyl, 2-methyl-2-propenyloxycarbonyl, 3-methyl-3-butenyloxycarbonyl, phenyloxycarbonyl, benzyloxycarbonyl, 1-phenylethoxycarbonyl, 2-phenylethoxycarbonyl, formyl, acetyl, propionyl, benzoyl, methylthio, ethylthio, methylsulphinyl, ethylsulphinyl, methylsulphonyl, ethylsulphonyl, phenylthio, phenylsulphinyl, phenylsulphonyl, formamido, acetamido, propionamido, trifluoroacetyl, trifluoroacetamido, N-methyltrifluoroacetamido, N-ethyltrifluoroacetamido, benzamido, N-methylbenzamido, N-ethylbenzamido, carbamoyl, N-methylcarbamoyl, N-ethylcarbamoyl, N,N-dimethylcarbamoyl, N,N-diethylcarbamoyl, phenylcarbamoyl, sulphamoyl, N-methylsulphamoyl, N-ethylsulphamoyl, N,N-dimethylsulphamoyl, N,N-diethylsulphamoyl, N-phenylsulphamoyl, methanesulphonamido, ethanesulphonamido, benzenesulphonamido, ureido, 3-methylureido, 3-ethylureido, 3-propylureido, 3-phenylureido, thioureido, 3-methylthioureido, 3-ethylthioureido and 3-propylthioureido; or $A^1$ is the group —NRaRb, in which Ra and Rb are independently selected from hydrogen, methyl, ethyl, propyl, benzyl, 1-phenylethyl, 2-phenylethyl, carboxymethyl, carboxyethyl, methoxycarbonylmethyl, methoxycarbonylethyl, ethoxycarbonylethyl, methoxycarbonylpropyl and ethoxycarbonylpropyl; or $A^1$ is the group —NRaRb, in which Ra and Rb when taken together complete a 1-pyrrolidinyl, 2-oxo-1-pyrrolidinyl, 1-piperidinyl or 2-oxo-1-piperidinyl ring;

$R^2$ is hydrogen, propoxy, isopropoxy, butoxy, 2-phenylpropoxy, 3-phenylpropoxy, cyano, methyl, ethyl, propyl, isopropyl, sec-butyl, aminomethyl, 2-aminoethyl, hydroxymethyl, 1-hydroxyethyl, 2-hydroxyethyl, methylaaminomethyl, methylaminoethyl, dimethylaminomethyl, 2-(dimethylamino)ethyl, vinyl, allyl, 1-propenyl, 2-butenyl, ethynyl, 1-propynyl, 2-propynyl, 1-butynyl, chloromethyl, bromomethyl, fluoromethyl, dichloromethyl, difluoromethyl, trifluoromethyl, 2,2,2-trifluoroethyl, pentafluoroethyl, methoxy, ethoxy, difluoromethoxy, trifluoroethoxy, 2,2,2-trifluoroethoxy, 3,3,3-trifluoropropoxy, vinyloxy, allyloxy, 1-propenyloxy, 2-butenyloxy, methoxymethyl, ethoxymethyl, 1-methoxyethyl, 2-methoxyethyl, 2-ethoxyethyl, 3-methoxypropyl, methylthiomethyl, 1-methylthioethyl, 2-methylthioethyl, 2-methylthioprop-2-yl, ethylthiomethyl, 1-ethylthioethyl, 2-ethylthioethyl, 2-ethylthioprop-2-yl, methylsulphinylmethyl, 1-methylsulphinylethyl, 2-methylsulphinylethyl, 2-methylsulphinylprop-2-yl, ethylsulphinylmethyl, 1-ethylsulphinylethyl, 2-ethylsulphinylethyl, 2-ethylsulphinylprop-2-yl, methylsulphonylmethyl, 1-methylsulphonylethyl, 2-methylsulphonylethyl, 2-methylsulphonylprop-2-yl, ethylsulphonylmethyl, 1-ethylsulphonylethyl, 2-ethylsulphonylethyl, 2-ethylsulphonylprop-2-yl, cyclopropyl, cyclobutyl, cyclopentyl, cyclopropylmethyl, cyclopropylethyl, cyclobutylmethyl, cyclopentylmethyl, phenyl, benzyl, 1-phenylethyl, 2-phenylethyl, phenoxy, benzyloxy, 1-phenylethoxy, 2-phenylethoxy, fluoro, chloro, bromo, iodo, hydroxy, mercapto, nitro, carboxy, methoxycarbonyl, ethoxycarbonyl, propoxycarbonyl, allyloxycarbonyl, 2-methyl-2-propenyloxycarbonyl, 3-methyl-3-butenyloxycarbonyl, phenyloxycarbonyl, benzyloxycarbonyl, 1-phenylethoxycarbonyl, 2-phenylethoxycarbonyl, fonnyl, acetyl, propionyl, benzoyl, methylthio, ethylthio, methylsulphinyl, ethylsulphinyl, methylsulphonyl, ethylsulphonyl, phenylthio, phenylsulphinyl, phenylsulphonyl, formamido, acetamido, propionamido, trifluoroacetyl, trifluoroacetamido, N-methyltrifluoroacetamido, N-ethyltrifluoroacetamido, benzamido, N-methylbenzamido, N-ethylbenzamido, carbamoyl, N-methylcarbamoyl, N-ethylcarbamoyl, N,N-dimethylcarbamoyl, N,N-diethylcarbamoyl, phenylcarbamoyl, sulphamoyl, N-methylsulphamoyl, N-ethylsulphamoyl, N,N-dimethylsulphamoyl, N,N-diethylsulphamoyl, N-phenylsulphamoyl, methanesulphonamido, ethanesulphonamido, benzenesulphonamido, ureido, 3-methylureido, 3-ethylureido, 3-propylureido, 3-phenylureido, thioureido, 3-methylthioureido, 3-ethylthioureido and 3-propylthioureido; or $R^2$ is the group —NRaRb, in which Ra and Rb are independently selected from hydrogen, methyl, ethyl, propyl, benzyl, 1-phenylethyl, 2-phenylethyl, carboxymethyl, carboxyethyl, methoxycarbonylmethyl, methoxycarbonylethyl, ethoxycarbonylethyl, methoxycarbonylpropyl and ethoxycarbonylpropyl; or $R^2$ is the group —NRaRb, in which Ra and Rb when taken together complete a 1-pyrrolidinyl, 2-oxo-1-pyrrolidinyl, 1-piperidinyl or 2-oxo-1-piperidinyl ring;

$R^1$ is selected from 2-methoxycarbonylethenyl, 2-ethoxycarbonylethenyl, 2-phenylethenyl, methoxycarbonylethynyl, ethoxycarbonylethynyl, phenylethynyl, methyl, ethyl, propyl, isopropyl, sec-butyl, aminomethyl, 2-aminoethyl, hydroxymethyl, 1-hydroxyethyl, 2-hydroxyethyl, methylaminomethyl, methylaminoethyl, dimethylaminomethyl, 2-(dimethylamino)ethyl, vinyl, allyl, 1-propenyl, 2-butenyl, ethynyl, 1-propynyl, 2-propynyl, 1-butynyl, chloromethyl, bromomethyl, fluoromethyl, dichloromethyl, difluoromethyl, trifluoromethyl, 2,2,2-trifluoroethyl, pentafluoroethyl, methoxy, ethoxy, difluoromethoxy, trifluoroethoxy, 2,2,2-trifluoroethoxy, 3,3,3-trifluoropropoxy, vinyloxy, allyloxy, 1-propenyloxy, 2-butenyloxy, methoxymethyl, ethoxymethyl, 1-methoxyethyl, 2-methoxyethyl, 2-ethoxyethyl, 3-methoxypropyl, methylthiomethyl, 1-methylthioethyl, 2-methylthioethyl, 2-methylthioprop-2-yl, ethylthiomethyl, 1-ethylthioethyl, 2-ethylthioethyl, 2-ethylthioprop-2-yl, methylsulphinylmethyl, 1-methylsulphinylethyl, 2-methylsulphinylethyl, 2-methylsulphinylprop-2-yl, ethylsulphinylmethyl, 1-ethylsulphinylethyl, 2-ethylsulphinylethyl, 2-ethylsulphinylprop-2-yl, methylsulphonylmethyl, 1-methylsulphonylethyl, 2-methylsulphonylethyl, 2-methylsulphonylprop-2-yl, ethylsulphonylmethyl, 1-ethylsulphonylethyl, 2-ethylsulphonylethyl, 2-ethylsulphonylprop-2-yl, cyclopropyl, cyclobutyl, cyclopentyl, cyclopropylmethyl, cyclopropylethyl, cyclobutylmethyl, cyclopentylmethyl, phenyl, benzyl, 1-phenylethyl, 2-phenylethyl, phenoxy, benzyloxy, 1-phenylethoxy, 2-phenylethoxy, fluoro, chloro, bromo, iodo, hydroxy, mercapto, nitro, carboxy, methoxycarbonyl, ethoxycarbonyl, propoxycarbonyl, allyloxycarbonyl, 2-methyl-2-propenyloxycarbonyl, 3-methyl-3-butenyloxycarbonyl, phenyloxycarbonyl, benzyloxycarbonyl, 1-phenylethoxycarbonyl, 2-phenylethoxycarbonyl, formyl, acetyl, propionyl, benzoyl, methylthio, ethylthio, methylsulphinyl, ethylsulphinyl, methylsulphonyl, ethylsulphonyl, phenylthio, phenylsulphinyl, phenylsulphonyl, formamido, acetamido, propionamido, trifluoroacetyl, trifluoroacetamido, N-methyltrifluoroacetamido, N-ethyltrifluoroacetamido, benzamido, N-methylbenzamido, N-ethylbenzamido, carbamoyl, N-methylcarbamoyl, N-ethylcarbamoyl, N,N-dimethylcarbamoyl, N,N-diethylcarbamoyl, phenylcarbamoyl, sulphamoyl, N-methylsulphamoyl, N-ethylsulphamoyl, N,N-dimethylsulphamoyl, N,N-diethylsulphamoyl, N-phenylsulphamoyl, methanesulphonamido, ethanesulphonamido, benzenesulphonamido, ureido, 3-methylureido, 3-ethylureido, 3-propylureido, 3-phenylureido, thioureido, 3-methylthioureido, 3-ethylthioureido and 3-propylthioureido; or $R^1$ is the group —NRaRb, in which Ra and Rb are independently selected from hydrogen, methyl, ethyl, propyl, benzyl, 1-phenylethyl, 2-phenylethyl, carboxymethyl, carboxyethyl, methoxycarbonylmethyl, methoxycarbonylethyl, ethoxycarbonylethyl, methoxycarbonylpropyl and ethoxycarbonylpropyl; or $R^1$ is the group —NRaRb, in which Ra and Rb when taken together complete a 1-pyrrolidinyl, 2-oxo-1-pyrrolidinyl, 1-piperidinyl or 2-oxo-1-piperidinyl ring;

any phenyl, naphthyl or benzene moiety of $A^1$, $R^1$ or $R^2$ is either unsubstituted or is substituted at one or two positions, with substituents independently selected at each occurrence from methyl, ethyl, methoxy, ethoxy, fluoro, chloro, bromo, iodo, cyano and trifluoromethyl.

3. A compound or pharmaceutically-acceptable salt according to claim 1, having the formula Ia;

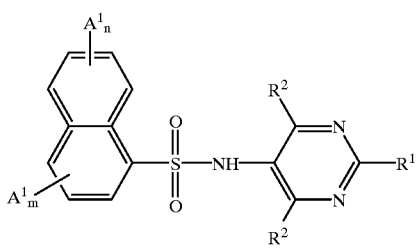

where $A^1$, $R^1$ and $R^2$ are as defined in claim 1, and each of n and m can have a value 0, 1, 2 or 3, provided that the value of (n+m) is not greater than 3.

4. A compound according to claim 3, selected from the group consisting of:
5-dimethylamino-N-(2,4-dimethoxy-5-pyrimidinyl)-1-naphthalenesulphonamide,
5-dimethylamino-N-(2-chloro-4-methoxy-5-pyrimidinyl)-1-naphthalenesulphonamide,
5-dimethylamino-N-(2-chloro-4-methylthio-5-pyrimidinyl)-1-naphthalenesulphonamide, and
5-dimethylamino-N-(2-bromo-5-pyrimidinyl)-1-naphthalenesulphonamide.

5. A compound or pharmaceutically-acceptable salt according to claim 1, having the formula Ib;

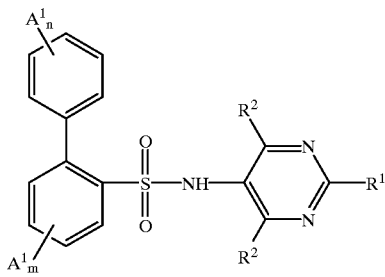

where $A^1$, $R^1$ and $R^2$ are as defined in claim 1, and each of n and m can have a value 0, 1, 2 or 3, provided that the value of (n+m) is not greater than 3.

6. A compound N-(2-chloro-4-methoxy-5-pyrimidinyl)-2-biphenylsulphonamide, according to claim 5.

7. A process for the manufacture of a compound of formula VII according to claim 1, said process comprising either:

(a) reacting an amine of the formula IVa;

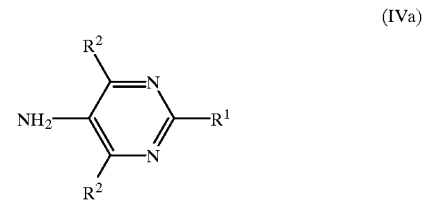

where $R^1$ and $R^2$ are as defined in claim 1, or an alkali metal salt thereof, with a sulphonyl halide of formula IVb;

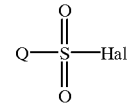

in which Hal is a halogeno group, or with a sulphonate of the formula IVc;

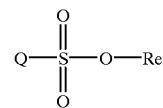

in which Re is an electron-deficient phenyl group; or, for a compound of formula VII in which Q is biphenyl;

(b) reacting a compound of the formula VI

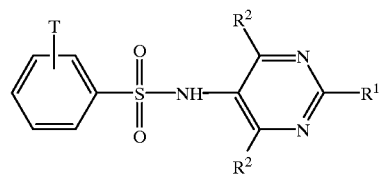

in which T is a bromo, an iodo or a trifluoromethanesulphonyloxy group and the T-bearing phenyl ring is either unsubstituted or substituted with an unsubstituted or substituted phenylboronic acid, or an anhydride or ester thereof, in the presence of a suitable base and a palladium(O), palladium (II), nickel(O) or nickel(II) catalyst; where any substituent on said T-bearing ring or on said phenylboronic acid is selected from any of the moieties defined as $A_1$ in claim 1, and that said T-bearing ring and said phenylboronic acid when taken together bear no more than three such substituents;

(c) removing a protecting group, if present; wherein:
if an optically-active form of a compound of formula VII is required, then the aforesaid processes (a)–(b) are carried out with an optically-active starting material, or the racemic form of a compound of formula VII is resolved; and
if a conversion of one compound of formula VII into another compound of formula VII is required, then said conversion is achieved by a conventional functional group interconversion.

8. A method of treating a disease or medical condition associated with hypertension, pulmonary hypertension, congestive heart-failure, dyslipidaemia, atherosclerosis, restenosis, acute or chronic renal-failure, ischaemic stroke, subarachnoid haemoffhage, intermittent claudication, critical limb ischaemia, asthma or organ-failure after general surgery or transplantation, in a human or other warm-blooded animal, said method comprising administering to said animal an effective amount of a compound or pharmacologically-acceptable salt according to claim 1.

9. A method of counteracting the effects of hypertension, pulmonary hypertension, congestive heart-failure, dyslipidaemia, atherosclerosis, restenosis, acute or chronic renal-failure, ischaemic stroke, subarachnoid haemorrhage, intermittent claudication, critical limb ischaemia, asthma or organ-failure after general surgery or transplantation, in a human or other warm-blooded animal, said method comprising administering to said animal an effective amount of a compound or pharmacologically-acceptable salt according to claim 1.

10. A compound or pharmaceutically-acceptable salt according to claim 1, having the formula VIIa;

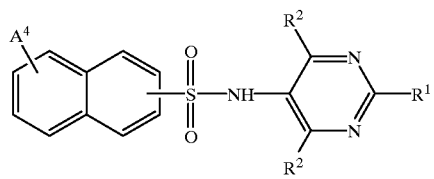

(VIIa)

wherein: $A^4$ is $C_1$–$C_4$-alkanoylamino or a group —NRaRb in which Ra and Rb are independently selected from hydrogen or $C_1$–$C_4$-alkyl, and where $R^1$ and $R^2$ are as defined in claim 1.

11. A compound according to claim 10, wherein the sulphonamido group is attached at the 1-position and the $A^4$ group is attached at the 5-position of the naphthyl ring.

12. A compound or pharmaceutically-acceptable salt according to claim 1, having the formula (VIIb);

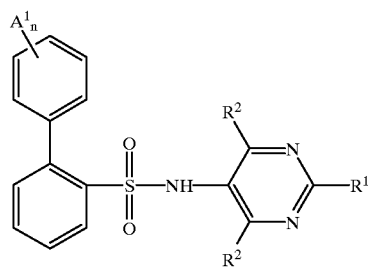

(VIIb)

wherein n is 1 or 2 and where $A^1$, $R^1$ and $R^2$ are as defined in claim 1.

13. A pharmaceutical composition comprising a compound according to claim 1, together with a pharmaceutically-acceptable excipient or diluent.

* * * * *